(12) United States Patent
Souls et al.

(10) Patent No.: US 12,011,161 B2
(45) Date of Patent: Jun. 18, 2024

(54) SUTURE NEEDLE ADAPTORS FOR DELIVERING SUTURE NEEDLES THROUGH CANNULAS WHILE SIMULTANEOUSLY VISUALIZING THE DELIVERY OF THE SUTURE NEEDLES THROUGH THE CANNULAS

(71) Applicant: Ethicon, Inc., Somerville, NJ (US)

(72) Inventors: Doug Souls, Andover, NJ (US); Robert Rousseau, Ottsville, PA (US); Alexander M. Cannara, Roseland, NJ (US); Noha Elmouelhi, Whitehouse Station, NJ (US); Jared Schneider, Union, NJ (US); Wayne Holloway, Phillipsburg, NJ (US)

(73) Assignee: Ethicon, Inc., Raritan, NJ (US)

( * ) Notice: Subject to any disclaimer, the term of this patent is extended or adjusted under 35 U.S.C. 154(b) by 566 days.

(21) Appl. No.: 17/154,088

(22) Filed: Jan. 21, 2021

(65) Prior Publication Data
US 2022/0225983 A1 Jul. 21, 2022

(51) Int. Cl.
*A61B 17/06* (2006.01)
*A61B 1/018* (2006.01)
(Continued)

(52) U.S. Cl.
CPC ........ *A61B 17/06066* (2013.01); *A61B 1/018* (2013.01); *A61B 1/05* (2013.01);
(Continued)

(58) Field of Classification Search
CPC ............ A61B 1/00013; A61B 1/00131; A61B 90/361; A61B 17/06066;
(Continued)

(56) References Cited

U.S. PATENT DOCUMENTS 5,219,358 A    6/1993  Bendel et al.
5,578,044 A *  11/1996 Gordon .............. A61B 17/0625
                                                606/147
(Continued)

FOREIGN PATENT DOCUMENTS

CN     201958934      9/2011
CN     201958941      9/2011
(Continued)

OTHER PUBLICATIONS

Resad Pasic, M.D., Ph.D., "All You Need To Know About Laparoscopic Suturing," A Practical Manual of Laparoscopic and Minimally Invasive Gynecology: A Clinical Cookbook, Second Edition, 2007, pp. 97-108, published by Informa Healthcare, United Kingdom.
(Continued)

*Primary Examiner* — Tan-Uyen T Ho
*Assistant Examiner* — Osama Nemer

(57) ABSTRACT

A needle camera adaptor includes a tube-shaped body having a proximal end, a distal end, a longitudinal axis, and a lumen that extends along the longitudinal axis. A centrally-located lateral access opening is formed in an outer wall of the tube-shaped body. A needle securing channel is formed in the outer wall and extends between the lateral access opening and the distal end of the tube-shaped body. A curved suture needle is disposed within the needle securing channel. The needle securing channel and the curved suture needle extend along an axis that defines an oblique angle with the longitudinal axis of the needle camera adaptor. A visualization device, facing distally, is positioned within the lumen at the proximal end of the tube-shaped body. The lateral access opening, the needle securing channel, and the curved suture needle are located within a field of view of the visualization device.

18 Claims, 22 Drawing Sheets

(51) Int. Cl.
*A61B 1/05* (2006.01)
*A61B 1/06* (2006.01)
*A61B 17/00* (2006.01)
*A61B 90/00* (2016.01)
*A61B 1/00* (2006.01)

(52) U.S. Cl.
CPC ...... *A61B 1/0661* (2013.01); *A61B 17/06128* (2013.01); *A61B 1/00013* (2013.01); *A61B 1/00131* (2013.01); *A61B 2017/00296* (2013.01); *A61B 2017/0034* (2013.01); *A61B 90/361* (2016.02)

(58) Field of Classification Search
CPC ...... A61B 2017/00296; A61B 17/0464; A61B 1/018; A61B 1/05; A61B 1/0661; A61B 17/06128; A61B 2017/0034; A61B 1/00098; A61B 1/00089; A61B 1/00101; A61B 2017/00907; A61B 2017/0608; A61B 2090/034; A61B 17/0483
See application file for complete search history.

(56) References Cited

U.S. PATENT DOCUMENTS

| | | | |
|---|---|---|---|
| 5,766,186 A * | 6/1998 | Faraz | A61B 17/0469 606/223 |
| 5,908,426 A | 6/1999 | Pierce | |
| 6,113,610 A | 9/2000 | Poncet | |
| 6,358,197 B1 * | 3/2002 | Silverman | A61F 2/04 600/29 |
| 6,527,793 B1 | 3/2003 | Valtchev | |
| 6,689,130 B2 * | 2/2004 | Arai | A61B 18/1492 606/46 |
| 6,730,061 B1 | 5/2004 | Cuschieri et al. | |
| 7,063,715 B2 * | 6/2006 | Onuki | A61B 17/0401 606/220 |
| 7,083,687 B2 | 8/2006 | Tanaka et al. | |
| 7,261,728 B2 * | 8/2007 | Long | A61B 10/04 600/153 |
| 7,270,720 B2 | 9/2007 | Brhel et al. | |
| 7,399,304 B2 * | 7/2008 | Gambale | A61B 17/0401 606/41 |
| 7,727,257 B2 | 6/2010 | Loubens et al. | |
| 7,922,744 B2 | 4/2011 | Morris et al. | |
| 8,057,386 B2 * | 11/2011 | Aznoian | A61B 1/00087 606/139 |
| 8,075,573 B2 * | 12/2011 | Gambale | A61B 17/0469 606/145 |
| 8,118,820 B2 * | 2/2012 | Stokes | A61B 17/0469 606/139 |
| 8,308,764 B2 | 11/2012 | Loubens et al. | |
| 8,480,689 B2 * | 7/2013 | Spivey | A61B 17/06066 606/147 |
| 8,545,521 B2 * | 10/2013 | McClurg | A61B 17/0482 606/139 |
| 8,784,382 B2 | 7/2014 | McGuckin et al. | |
| 8,821,518 B2 * | 9/2014 | Saliman | A61B 17/0469 606/205 |
| 8,915,932 B2 | 12/2014 | Pipenhagen et al. | |
| 9,526,570 B2 * | 12/2016 | McLawhorn | A61B 18/1485 |
| 9,610,075 B2 | 4/2017 | Heneveld | |
| 10,398,461 B2 * | 9/2019 | Bhatt | A61B 18/1492 |
| 10,791,911 B2 * | 10/2020 | Wales | A61B 1/00137 |
| 2002/0116010 A1 * | 8/2002 | Chung | A61B 17/0469 606/139 |
| 2003/0009085 A1 | 1/2003 | Arai et al. | |
| 2004/0147941 A1 * | 7/2004 | Takemoto | A61B 17/0625 606/144 |
| 2006/0282090 A1 * | 12/2006 | Stokes | A61B 1/0014 606/144 |
| 2006/0282096 A1 * | 12/2006 | Papa | A61B 1/0014 606/144 |
| 2006/0282098 A1 * | 12/2006 | Shelton | A61B 1/00094 606/144 |
| 2007/0066870 A1 | 3/2007 | Ohashi et al. | |
| 2007/0203395 A1 * | 8/2007 | Mikkaichi | A61B 1/00089 600/129 |
| 2011/0125108 A1 | 5/2011 | Deviere et al. | |
| 2011/0172706 A1 | 7/2011 | Kappel et al. | |
| 2016/0193023 A1 | 7/2016 | Pereira et al. | |
| 2016/0281199 A1 | 9/2016 | Loubens | |
| 2016/0338696 A1 | 11/2016 | Loubens | |
| 2017/0112361 A1 * | 4/2017 | Surti | A61B 1/00101 |
| 2017/0252038 A1 | 9/2017 | Callaghan et al. | |
| 2018/0042603 A1 * | 2/2018 | Mitelberg | A61B 90/57 |
| 2018/0110511 A1 * | 4/2018 | O'Hara | A61B 17/06066 |
| 2019/0365380 A1 * | 12/2019 | Holton | A61B 17/0485 |
| 2019/0374217 A1 | 12/2019 | Hernandez et al. | |
| 2020/0268382 A1 * | 8/2020 | Vailhe | A61B 17/06114 |
| 2020/0360011 A1 * | 11/2020 | Deuel | A61B 17/0469 |

FOREIGN PATENT DOCUMENTS

| | | |
|---|---|---|
| CN | 102551830 | 7/2012 |
| CN | 204410871 | 6/2015 |
| DE | 102004012680 | 11/2005 |
| EP | 2781194 | 9/2014 |
| JP | 2010-094367 | 4/2010 |
| WO | 9508296 | 3/1995 |
| WO | 2018/006044 | 1/2018 |

OTHER PUBLICATIONS

"Telescopes, Visualization and Documentation Systems for Video-Assisted Cardiac Surgery and Open Heart Surgery with Minimal Access," Karl Storz Endoscope, Karl Storz SE & Co. KG, Tuttlingen, Germany, www.karlstorz.com, 24 pages.

* cited by examiner

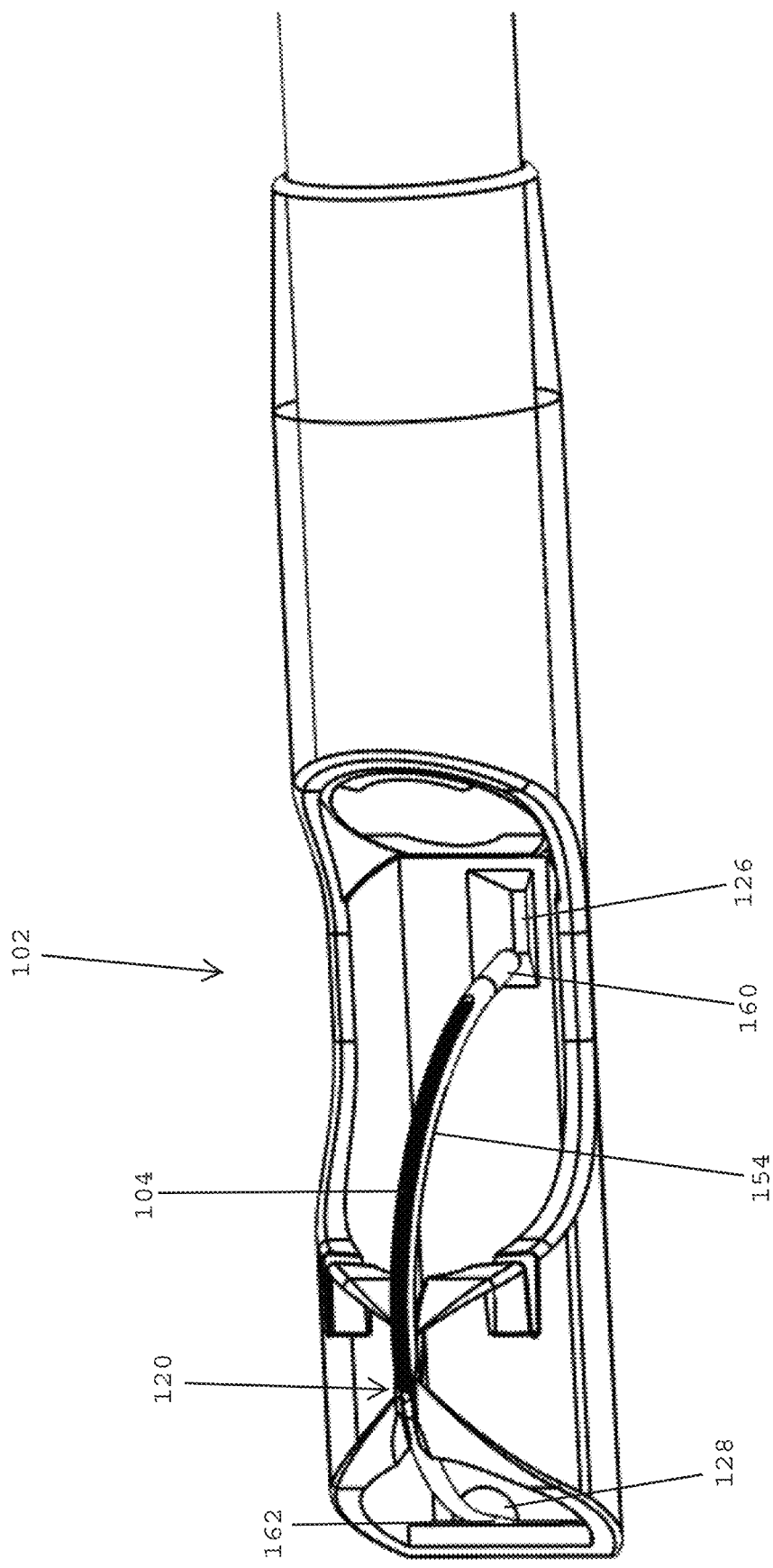

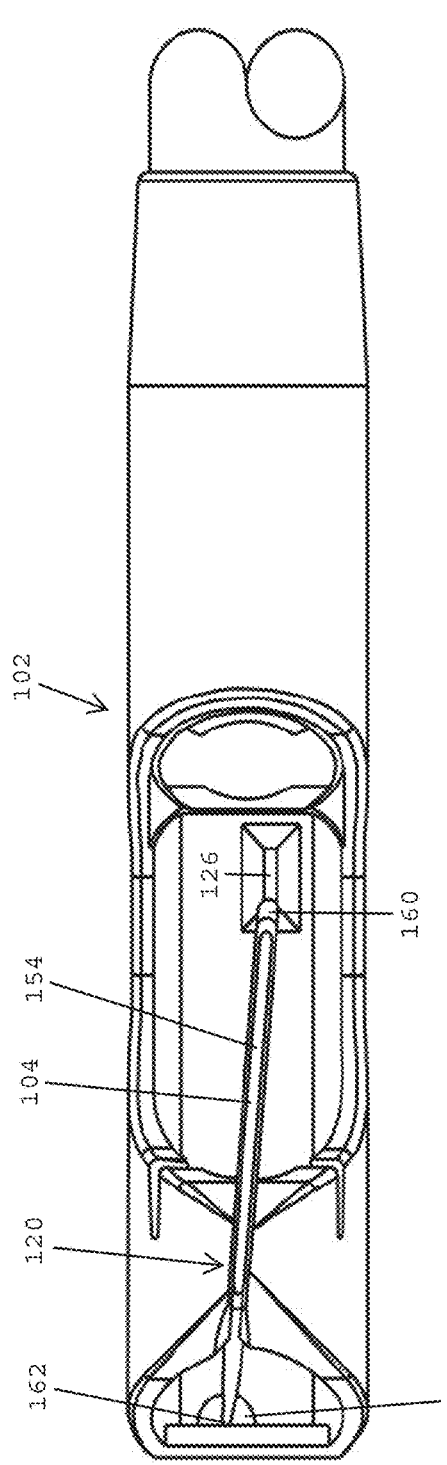
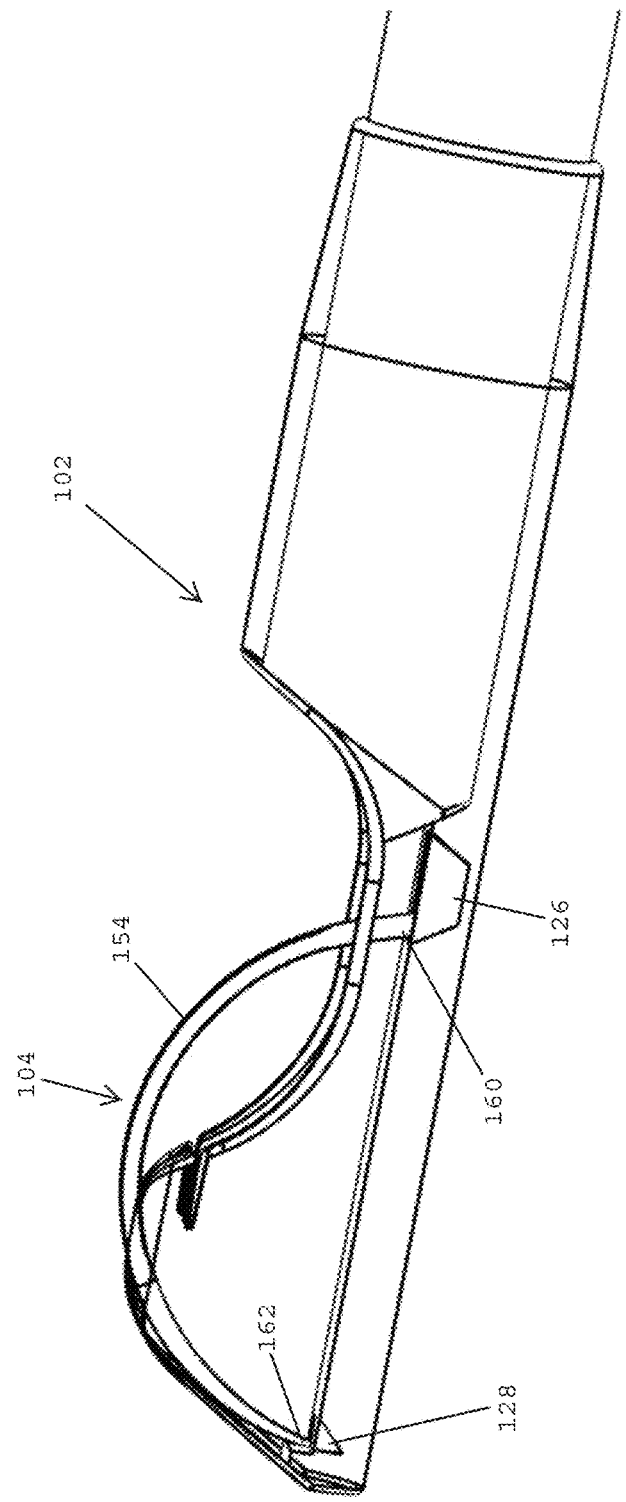
FIG. 6B
FIG. 6C

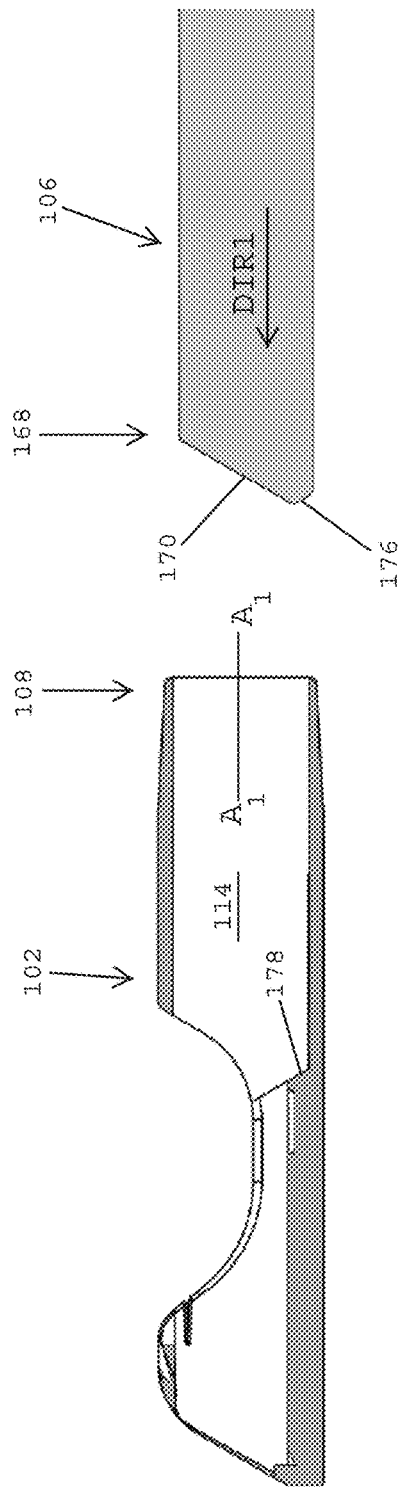
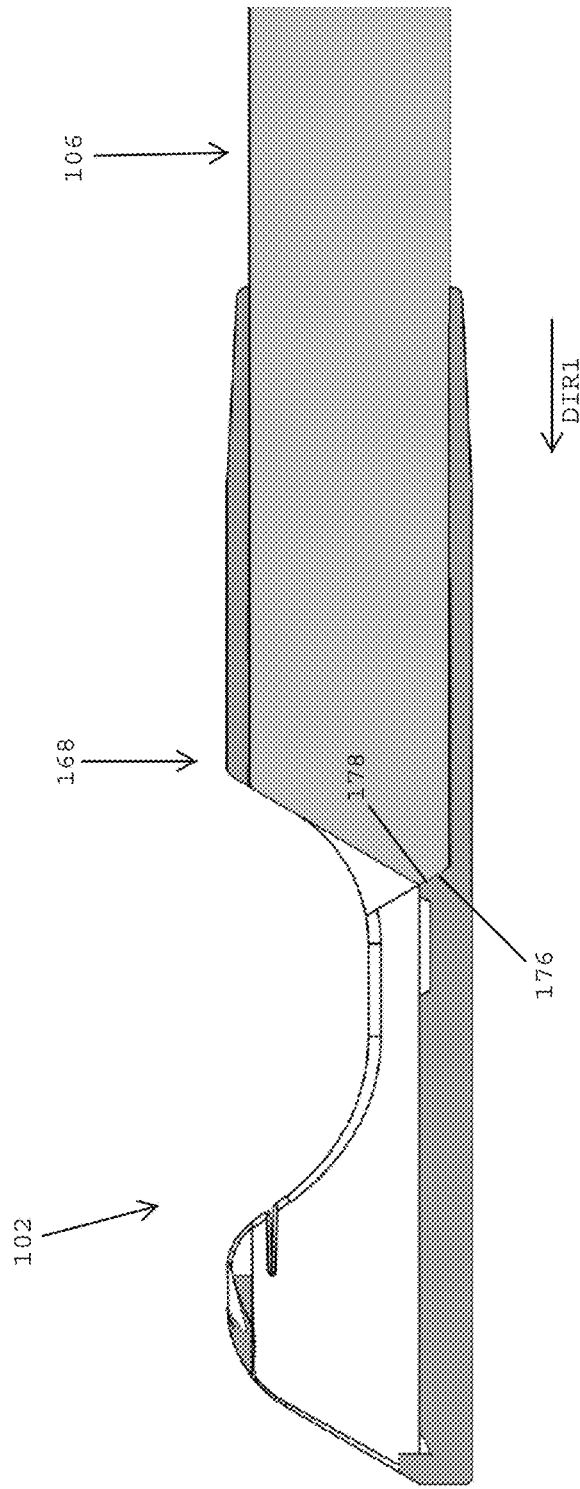
FIG. 9A
FIG. 9B

SUTURE NEEDLE ADAPTORS FOR DELIVERING SUTURE NEEDLES THROUGH CANNULAS WHILE SIMULTANEOUSLY VISUALIZING THE DELIVERY OF THE SUTURE NEEDLES THROUGH THE CANNULAS

BACKGROUND OF THE INVENTION

Field of the Invention

The present patent application is generally related to surgical instruments, and is more specifically related to surgical instruments used for delivering suture needles through cannulas for use at surgical sites.

Description of the Related Art

Sutures are used to approximate tissue that has been separated during a surgical procedure or due to an accident or trauma. Instruments used for suturing tissue typically include a suture needle and a trailing length of suture thread that is attached to an end of the suture needle.

In order to minimize patient trauma during minimally invasive surgical (MIS) procedures, many efforts have been directed to reducing the size (e.g., the diameter) of the trocars and cannulas (hereinafter commonly referred to as cannulas) that are inserted into patients. When a surgical procedure requires suturing tissue, a problem arises in the types of needle and suture assemblies that can be delivered through the cannula to the surgical site. Many surgeons prefer to use curved needles, which are typically in the range of ¼ to ⅝ of a circle (i.e., an arc whose interior angle is in the range of about 90 degrees-225 degrees). Curved needles having these dimensions require the cannula to be large enough to accommodate the needle, as well as the instrument(s) necessary to deliver the needle within the surgical space, to ensure a safe and controlled delivery of the sharp needle within the endoscopic space. In many instances, the combined size of the curved surgical needle and the delivery instrument is too large so that the curved surgical needle and the delivery instrument cannot be passed through the narrower cannula to reach the surgical site.

Constraints on the size of the cannula or trocar create challenges when selecting instruments and devices that are used for accessing invasive surgical spaces. When introducing a curved suture needle, in a controlled fashion, the delivery instrument and the largest size needle is limited to what will fit within a cannula typically having an interior diameter in a range from 5 mm to 15 mm.

Methods of passing suture needles into peritoneal spaces without the using cannulas have been disclosed. For example, Dr. H. Reich disclosed a method for introducing any size curved needle into the peritoneal cavity through a 5 mm lower quadrant incision in an article entitled, "All You Need to Know About Laparoscopic Suturing," in the book *A Practical Manual of Laparoscopy and Minimally Invasive Gynecology—A Clinical Cookbook*, second edition, 2007, by Resad Pasic, M.D., Ph.D. As disclosed by Dr. H. Reich, a 5 mm trocar is withdrawn from the abdomen of a patient. A grasper is passed through the withdrawn 5 mm trocar cannula and the suture is grasped slightly away from the needle base. The grasper is then forced into the unoccupied trocar cannula incision with the needle trailing alongside the grasper. The trocar cannula is also passed back through the incision along with the grasper. The disadvantage of this method is that insertion of the needle into the abdominal wall, after the removal of the trocar sleeve, makes it difficult for the surgeon to find the original incision resulting in additional damage as he or she attempts to follow the original path. Also, the unprotected needle point may damage the soft tissue, vessels, and nerves as the needle travels through the soft tissue.

Another method for introducing a large curved needle through a small cannula involves forcibly bending the needle at a distinct location to flatten the arc of the needle. The semi-flattened needle is then passed through the cannula and is subsequently manually bent back into the larger arced configuration prior to use within the endoscopic space. This manipulation of the surgical needle results in malformed arced geometries that are more difficult to guide, damaged needle points, and an increased likelihood that the bent needle will break because the curved needles are not designed to be altered (e.g., bent).

U.S. Pat. No. 6,527,793 to Valtchev discloses a device for introducing and removing a laparoscopic needle through an incision in a wall of a body cavity. The device includes a rod unit with an elongated rod member having proximal and distal end segments that are disposed on opposite ends of an interior chamber. The interior chamber has an elongated slot that is dimensioned to receive a curved laparoscopic needle and a handle member for manipulating the position of the laparoscopic needle within the body cavity. The device provides a mechanism for placing the needle within the cavity directly through the incision, similar to that as disclosed by Dr. H. Reich, however, it protects the ends of the needle from contacting the tissue during passage through the incision. Like the Reich method, the device requires the removal of the cannula, however, due to the presence of the rod geometry, the back span of the needle must dilate the tissue incision to compensate for the shortening of the incision length due to the accommodation of the rod volume.

U.S. Pat. No. 5,219,358 to Bendel et. al. discloses a surgical needle made of a shape memory alloy, which has a first, low temperature state and a second, high temperature state, and methods for using the surgical needle. The shape memory alloy has a low temperature state, in which the needle is formable into an elongated shape to pass through an elongated tube, and a high temperature state, in which the needle forms an arc. The needle is particularly adapted for use in endoscopic surgery. A needle that has a curved shape is straightened and passed to a surgical site through a cannula. It is then returned to its curved shape by heating it at the surgical site. After use, the needle is withdrawn through the cannula. While the shape memory alloy needle provides a methodology for passing surgical needles with large geometries through smaller diameter cannulas, the methods of manufacture require revised tooling as well as increased manufacturing costs.

Accordingly, there remains a need for improved systems, devices and methods for passing curved suture needles through smaller diameter cannulas in a controlled and safe manner.

SUMMARY OF THE INVENTION

In one embodiment, a needle camera adaptor is designed for delivering a suture needle through a cannula while simultaneously visualizing the suture needle during passage through the cannula and subsequent placement within a surgical site. In one embodiment, the suture needle may be a curved suture needle and may have a suture thread secured to an end thereof. In one embodiment, the needle camera adaptor is configured for removing a curved suture needle (and the attached suture) through a cannula while simultaneously visualizing the suture needle and the suture.

In the prior art, before a suture needle may be passed through a cannula for being placed at a surgical site, the camera must first be removed from the cannula. As a result, the suture needle is passed through the cannula without visibility, and the camera may only be re-introduced into the cannula after the suture needle has been positioned at the surgical site. In contrast, in one embodiment of the present patent application, the needle camera adaptor preferably enables a suture needle to be passed through a cannula for placement at a surgical site, while maintaining continuous visualization of the suture needle at all times. In addition, the needle camera adaptor may be used for removing the suture needle from the surgical site while maintaining continuous visualization of the suture needle as it is removed through the cannula.

In one embodiment, a needle camera adaptor preferably includes an elongated body having a proximal end, a distal end, and a longitudinal axis that extends from the proximal end to the distal end thereof. The terms proximal and distal are defined as relative to the location of the instrument user, wherein proximal refers to structure that is closer to the user and distal refers to structure that is further away from the user and/or closer to the working end of the instrument. In one embodiment, the elongated body includes a tube-shaped outer wall that extends from the proximal end to the distal end of the elongated body, and a lumen that extends along the longitudinal axis of the elongated body from the proximal end to the distal end thereof.

In one embodiment, the needle camera adaptor desirably includes a lateral access opening formed in the tube-shaped outer wall that provides lateral access to the lumen. In one embodiment, the lateral access opening is located in a central region of the elongated body, which is preferably between the proximal and distal ends of the elongated body.

In one embodiment, a needle securing channel is preferably formed in the tube-shaped outer wall of the elongated body. In one embodiment, the needle securing channel extends between the lateral access opening and the distal end of the elongated body. In one embodiment, the needle securing channel extends along an axis that defines an oblique angle with the longitudinal axis of the elongated body.

In one embodiment, the needle camera adaptor desirably includes a visualization device that is positioned within the lumen of the elongated body, at the proximal end of the elongated body. In one embodiment, the lateral access opening and the needle securing channel are located within a field of view of the visualization device.

In one embodiment, the visualization device preferably includes an endoscope, which may be flexible or rigid, and which may be made of metal or polymer materials.

In one embodiment, the visualization device may include a camera for capturing images, and one or more lighting elements (e.g., fiber optic lights; LEDs) for illuminating the field of view of the visualization device.

In one embodiment, the needle camera adaptor preferably includes a proximal needle securing recess formed in an inner surface of the tube-shaped outer wall that is located within the central region of the elongated body, and a distal needle securing recess formed in the inner surface of the tube-shaped outer wall that is located adjacent the distal end of the elongated body. In one embodiment, the axis of the needle securing channel desirably extends between and is aligned with the proximal and distal needle securing recesses.

In one embodiment, the proximal needle securing recess is off-set from the longitudinal axis of the elongated body, and the distal needle securing recess is in alignment with the longitudinal axis of the elongated body.

In one embodiment, the needle camera adaptor may include a curved suture needle having a proximal end with a suture attachment barrel, a distal end with a sharpened tip, and a curved elongated body extending from the proximal end to the distal end of the curved suture needle.

In one embodiment, the proximal end of the curved suture needle may be disposed within the proximal needle securing recess, the distal end of the curved suture needle may be disposed within the distal needle securing recess, and the curved elongated body may be disposed within the needle securing channel for releasably securing the curved suture needle to the needle camera adaptor.

The distal needle securing recess preferably seats the sharpened tip of a curved suture needle and prevents accidental needle sticks from puncturing tissues, such as bowel, upon insertion into the surgical site. The distal needle securing recess also preferably provides protection for the needle tip from damage due to drag in the cannula and protects the trocar or cannula seal from damage due to needle punctures/rips.

In one embodiment, the needle securing channel preferably includes an elongated gap formed in the tube-shaped outer wall of the elongated body that extends from an outer surface to the inner surface of the tube-shaped outer wall. The needle securing channel desirably includes one or more resilient elements (e.g., scalloped features) that project into the gap that are adapted to provide a compressive force on lateral sides of the curved elongated body of the curved suture needle when the curved suture needle is disposed within the needle securing channel for releasably securing the curved suture needle within the needle securing channel.

In one embodiment, the curved elongated body of the curved suture needle that is disposed within the needle securing channel extends along the axis that defines the oblique angle with the longitudinal axis of the elongated body. As a result, the visualization device is able to obtain images of the side of the curved suture needle as it is passed through a cannula to a surgical site. This side image adds depth perception, which allows the needle to be easily grasped by the needle driver.

In one embodiment, the needle camera adaptor may have a distal stop located between the distal needle securing recess and the distal end of the elongated body for preventing the sharpened tip of the curved suture needle from moving distal to the distal end of the elongated body.

In one embodiment, a first end of a suture may be secured to the suture attachment barrel of the curved suture needle. In one embodiment, when the curved suture needle has been secured within the needle securing channel, and the suture attachment barrel is disposed within the proximal needle securing recess, the suture may extend out of the proximal needle securing recess, through the lateral access opening, and toward the proximal end of the elongated body of the needle camera adaptor.

In one embodiment, the needle camera adaptor may include at least one suture retrieval slot formed in the tube-shaped outer wall of the elongated body. In one embodiment, the at least one suture retrieval slot has an open end that is in communication with the lateral access opening, which faces toward the visualization device, and a closed end that is distal to the open end. In one embodiment, the at least one suture retrieval slot narrows between the open end and the closed end thereof.

In one embodiment, the at least one suture retrieval slot and the suture captured within the at least one suture retrieval slot are desirably disposed within a field of view of the visualization device.

In one embodiment, the needle camera adaptor may include one or more suture retrieval slots (e.g., two suture retrieval slots). In one embodiment, a first suture retrieval slot may be formed in the tube-shaped outer wall on a first lateral side of the elongated body, and a second suture retrieval slot may be formed in the tube-shaped outer wall on a second lateral side of the elongated body.

In one embodiment, the one or more suture retrieval slots are preferably located adjacent an upper end and/or top side of the tube-shaped outer wall of the elongated body of the needle camera adaptor, as opposed to a mid-section of the tube-shaped outer wall. If the one or more suture retrieval slots were positioned in the mid-section of the tube-shaped outer wall, during removal of a suture needle from a cannula, the suture strand material would be much more likely to catch on the overlapping seal flaps inside the head of the cannula. Thus, placing the suture retrieval slots at the upper end and/or top side of the tube-shaped outer wall, as well as proper shaping of the suture retrieval slots, desirably prevents the suture strand material from snagging and/or getting hung up on the seal flaps during removal of the suture needle from the cannula.

In one embodiment, the needle camera adaptor preferably includes a sloping distal end face that extends between the distal end of the elongated body and a distal end of the needle securing channel.

In one embodiment, a needle camera adaptor preferably includes a tube-shaped body having a proximal end, a distal end, a longitudinal axis that extends from the proximal end to the distal end, and a lumen that extends along the longitudinal axis of the tube-shaped body from the proximal end to the distal end thereof.

In one embodiment, the needle camera adaptor preferably has a lateral access opening formed in an outer wall of the tube-shaped body that provides lateral access to the lumen. The lateral access opening is desirably located in a central region of the tube-shaped body, which is preferably between the proximal and distal ends of the tube-shaped body.

In one embodiment, the needle camera adaptor preferably includes a needle securing channel formed in the outer wall of the tube-shaped body that extends between the lateral access opening and the distal end of the tube-shaped body. In one embodiment, the needle securing channel extends along an axis that is not parallel to the longitudinal axis. In one embodiment, the needle securing channel extends along an axis that defines an oblique angle with the longitudinal axis of the tube-shaped body.

In one embodiment, a curved suture needle is preferably disposed within the needle securing channel and may be accessible via the lateral access opening.

In one embodiment, the needle securing channel and the curved suture needle preferably extend along an axis that defines an oblique angle with the longitudinal axis of the tube-shaped body.

In one embodiment, the needle camera adaptor preferably includes a visualization device positioned within the lumen at the proximal end of the tube-shaped body and facing toward the distal end of the tube-shaped body. In one embodiment, the lateral access opening, the needle securing channel, and the curved suture needle secured within the needle securing channel are desirably located within a field of view of the visualization device.

In one embodiment, the visualization device preferably includes an endoscope having a distal end that is assembled with the proximal end of the tube-shaped body, a camera, and one or more lighting elements (e.g., an optical fiber; an LED) for illuminating the field of view of the visualization device.

In one embodiment, a needle camera adaptor may include a proximal needle recess formed in an inner surface of the tube-shaped body that is located within the central region of the tube-shaped body and that is adapted to seat a proximal end of the curved suture needle.

In one embodiment, a needle camera adaptor may include a distal needle recess formed in the inner surface of the tube-shaped body that is located adjacent the distal end of the tube-shaped body and that is adapted to seat a distal end of the curved suture needle.

In one embodiment, the axis of the needle securing channel extends between and is aligned with the proximal and distal needle recesses.

In one embodiment, the curved suture needle desirably includes the proximal end with a suture attachment barrel, the distal end with a sharpened tip, and a curved elongated body extending from the proximal end to the distal end of the curved suture needle. In one embodiment, the curved elongated body is disposed within the needle securing channel.

In one embodiment, the needle camera adaptor preferably has at least one suture retrieval slot formed in the outer wall of the tube-shaped body. The at least one suture retrieval slot preferably has an open end that is in communication with the lateral access opening and that faces toward the visualization device and a closed end that is distal to the open end. In one embodiment, the at least one suture retrieval slot narrows between the open end and the closed end thereof. In one embodiment, the needle camera adaptor preferably includes one or more suture retrieval slots. In one embodiment, the needle camera adaptor may include a pair of suture retrieval slots, wherein a first slot is located on a first lateral side of the outer wall and a second slot is located on a second lateral side of the outer wall.

In one embodiment, a needle camera adaptor may include a tube-shaped body having a proximal end, a distal end, a longitudinal axis that extends from the proximal end to the distal end, and a lumen that extends along the longitudinal axis of the tube-shaped body from the proximal end to the distal end thereof.

In one embodiment, a needle camera adaptor preferably includes a lateral access opening formed in an outer wall of the tube-shaped body that provides lateral access to the lumen of the tube-shaped body. In one embodiment, the lateral access opening is preferably located in a central region of the tube-shaped body that is between the proximal and distal ends of the tube-shaped body.

In one embodiment, a needle securing channel may be formed in the outer wall of the tube-shaped body. In one embodiment, the needle securing channel desirably extends between the lateral access opening and the distal end of the tube-shaped body.

In one embodiment, the needle camera adaptor preferably includes a proximal needle securing recess formed in an inner surface of the outer wall. In one embodiment, the proximal needle securing recess is located within the central region of the tube-shaped body and is off-set from the longitudinal axis.

In one embodiment, a needle camera adaptor preferably includes a distal needle securing recess formed in the inner surface of the outer wall, whereby the distal needle securing recess is located adjacent the distal end of the tube-shaped body and is in alignment with the longitudinal axis.

In one embodiment, the axis of the needle securing channel may extend between, intersect with, and/or be aligned with the proximal and distal needle securing recesses.

In one embodiment, a needle camera adaptor preferably includes at least one suture retrieval slot formed in the outer wall of the tube-shaped body. In one embodiment, the at least one suture retrieval slot preferably has an open end that is in communication with the lateral access opening and that faces toward the proximal end of the tube-shaped body and a closed end that is distal to the open end.

In one embodiment, the lateral access opening may be located between the visualization device and the distal end of the elongated body.

In one embodiment, the proximal needle securing recess may be located distal to the visualization device and opposite the lateral access opening.

In one embodiment, the proximal needle securing recess preferably accommodates the proximal end of a suture needle with a suture attached so as to not damage the suture.

In one embodiment, the proximal needle securing recess is desirably positioned off-set to a central axis that passes through the elongated member.

In one embodiment, the distal needle securing recess desirably provides optimum positioning of a curved suture needle to facilitate arming with a needle driver.

In one embodiment, the needle camera adaptor preferably maintains physical control of the suture needle during the passage of the suture needle and the visualization device (e.g., a camera) through a cannula (e.g., a trocar).

In one embodiment, the needle camera adaptor provides a visualization pathway. In one embodiment, the needle is visible during delivery under one focal length and the needle camera adaptor does not interfere with visualization under a longer focal length.

In one embodiment, the distal end of the needle camera adaptor preferably has a ramped or sloping distal end face, which provides for smoother entry of the distal end of the needle camera adaptor into a cannula.

In one embodiment, the needle camera adaptor preferably includes one or more suture engagement channels, which enable secure grasping of the suture to facilitate needle removal after use during a surgical procedure.

These and other preferred embodiments of the present patent application will be described in more detail below.

BRIEF DESCRIPTION OF THE DRAWINGS

FIG. 6A is a perspective view of a top side of a needle camera adaptor and a curved surgical suture needle secured to the needle camera adaptor, in accordance with one embodiment of the present patent application.

FIG. 6B is a top plan view of the needle camera adaptor and the curved surgical needle shown in FIG. 6A.

FIG. 6C is a side view of the needle camera adaptor and the curved surgical needle shown in FIGS. 6A and 6B with walls of the needle camera adaptor being partially transparent.

FIG. 9A illustrates a stage of a method of assembling a needle camera adaptor with a distal end of an endoscope, wherein the needle camera adaptor and the endoscope are shown in cross-section, in accordance with one embodiment of the present patent application.

FIG. 9B illustrates another stage of a method of assembling a needle camera adaptor with a distal end of an endoscope, wherein the needle camera adaptor and the endoscope are shown in cross-section, in accordance with one embodiment of the present patent application.

DETAILED DESCRIPTION OF PREFERRED EMBODIMENTS

Figure 1A:
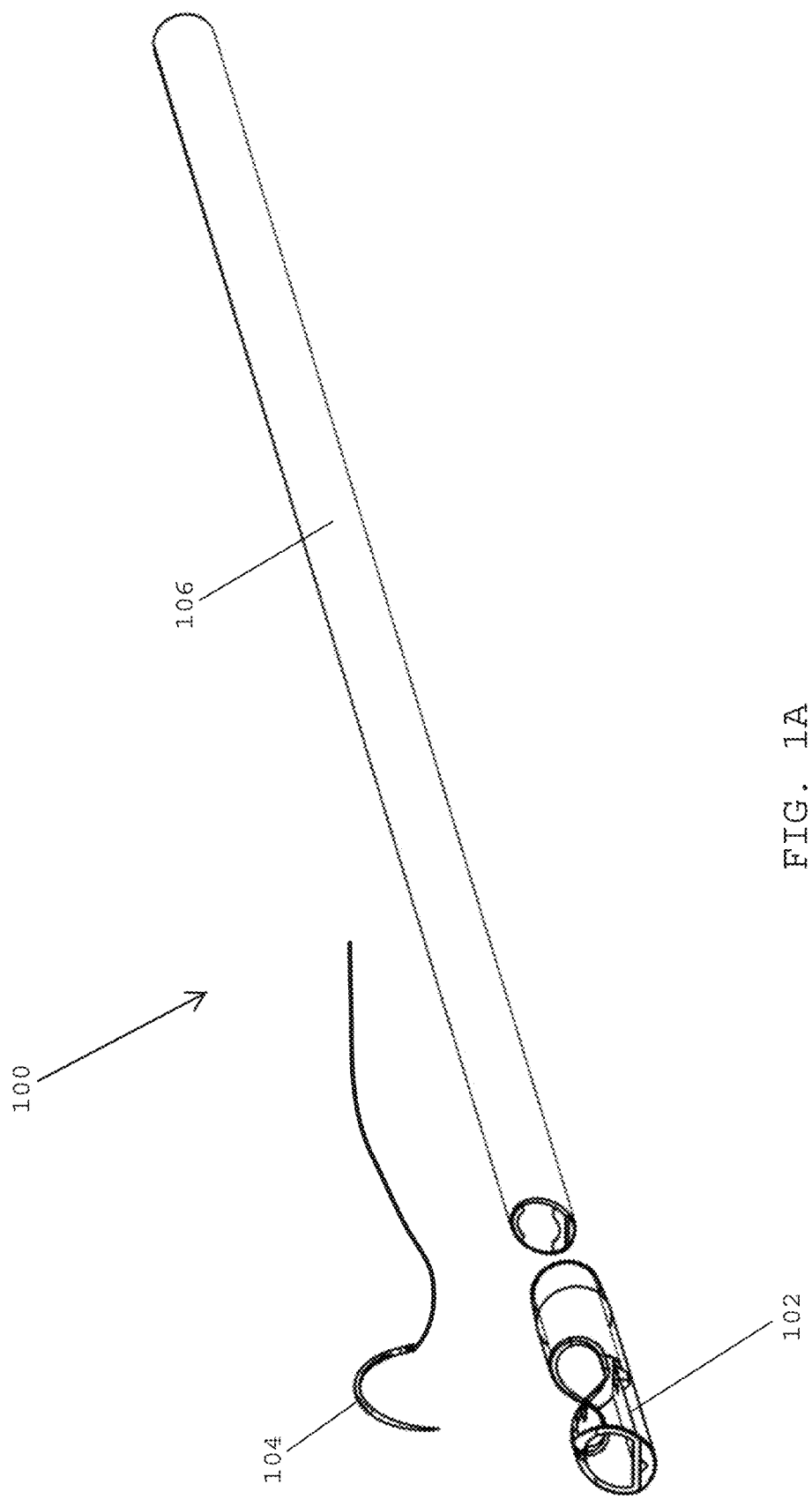
FIG. 1A is an exploded view of a system for delivering a suture needle through a cannula while simultaneously visualizing the suture needle during passage through the cannula including a needle camera adaptor, a surgical suture needle with a suture thread that is secured to the needle camera adaptor, and an endoscope/laparoscope that is adapted for being assembled with the needle camera adaptor, in accordance with one embodiment of the present patent application.

The systems, devices and methods disclosed herein teach instruments and methodologies for delivering a suture needle (e.g., a curved suture needle) and a suture (e.g., a suture strand) through a cannula and into an endoscopic surgical site while fully protecting the suture needle and simultaneously visualizing the suture needle during passage through the cannula. The systems, devices and methods disclosed herein are preferably designed to not interfere with the functionality of the surgical endoscope throughout the procedure. In addition, the systems, devices and methods preferably ensure that suture needles may be safely removed from the endoscopic workspace in a fully visualized and safe method. Unlike other systems and methods that lose sight of the suture needle during either the introduction or removal steps, the use of the needle camera adaptor disclosed herein ensures that the suture needle will always remain in sight of medical personnel so that the possibility of a dropped or lost suture needle is eliminated.

As used herein, the terms surgical needle and suture needle are used interchangeably. A surgical needle may have a suture attached thereto or may not have a suture attached thereto. A suture needle may have a suture attached thereto or may not have a suture attached thereto. Regardless of whether the terms surgical needle or suture needle are used herein, the terms may be used to describe both needles having sutures attached thereto and needles that do not have sutures attached thereto.

As used herein, the term cannula means a tube that is inserted into a body cavity to administer medicine, drain off fluid, and/or insert a surgical instrument.

As used herein, a trocar means a surgical instrument including a cannula, a seal at a proximal end of the cannula, and an obturator (e.g., a metal or plastic rod-like element with a sharpened or non-bladed tip) at a distal end of the cannula. During endoscopic surgery, trocars are inserted through the abdominal wall for the purpose of viewing and/or performing surgery in the abdominal or pelvic cavities. The trocar functions as a portal for the subsequent placement of other instruments, such as needle drivers, graspers, and staplers. In the present patent application, the terms trocar and cannula may be used interchangeably.

As used herein, an endoscope means an illuminated flexible or rigid tubular instrument for visualizing inside a body cavity or the interior of a hollow organ or part (e.g., a bladder) for diagnostic or treatment purposes, including more specifically, laparoscopes. An endoscope may have one or more channels that enable surgical instruments to be passed through the endoscope for treating a patient. An endoscope may be inserted through a natural passageway (e.g., the esophagus) or through a small surgical opening formed in the skin or through a cannulated instrument, such as a trocar device. In one embodiment, an endoscope preferably includes a small camera with a light at the end of a cable for transmitting images to a video monitor. A surgeon may use special instruments that work through one of the channels of the endoscope alongside the cable used for transmitting images.

Figure 1B:
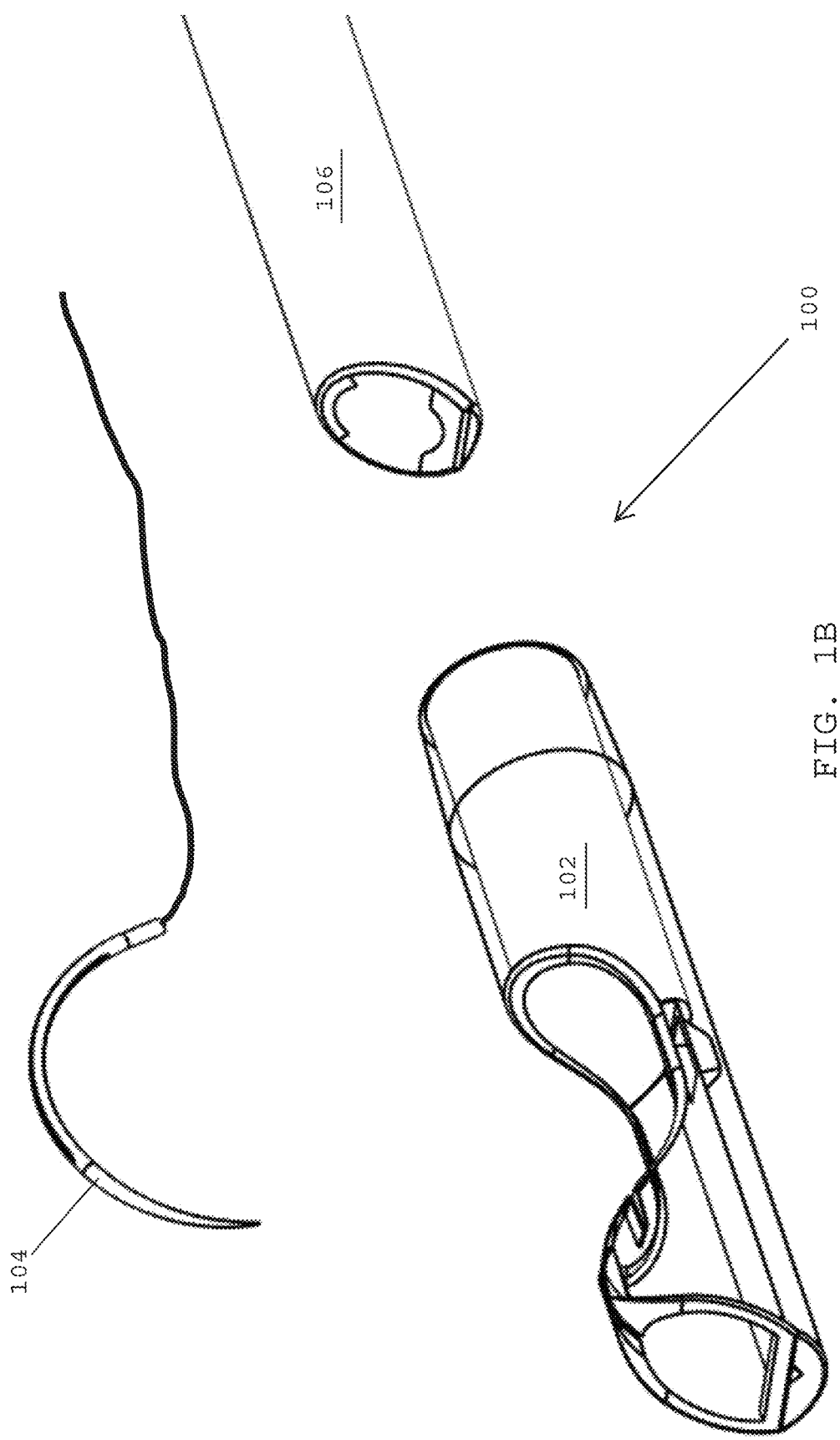
FIG. 1B is a magnified view of the needle camera adaptor, the surgical suture needle, and the distal end of the endoscope shown in FIG. 1A.

Referring to FIGS. 1A and 1B, in one embodiment, a system 100 for delivering a suture needle through a cannula to a surgical site preferably includes a needle camera adaptor 102, a suture needle 104, and an endoscope 106. The suture needle 104 may be an armed surgical needle including a suture thread secured to a proximal end of the surgical needle. In one embodiment, the suture needle may be a curved surgical needle that is used for suturing tissue.

Figure 2A:
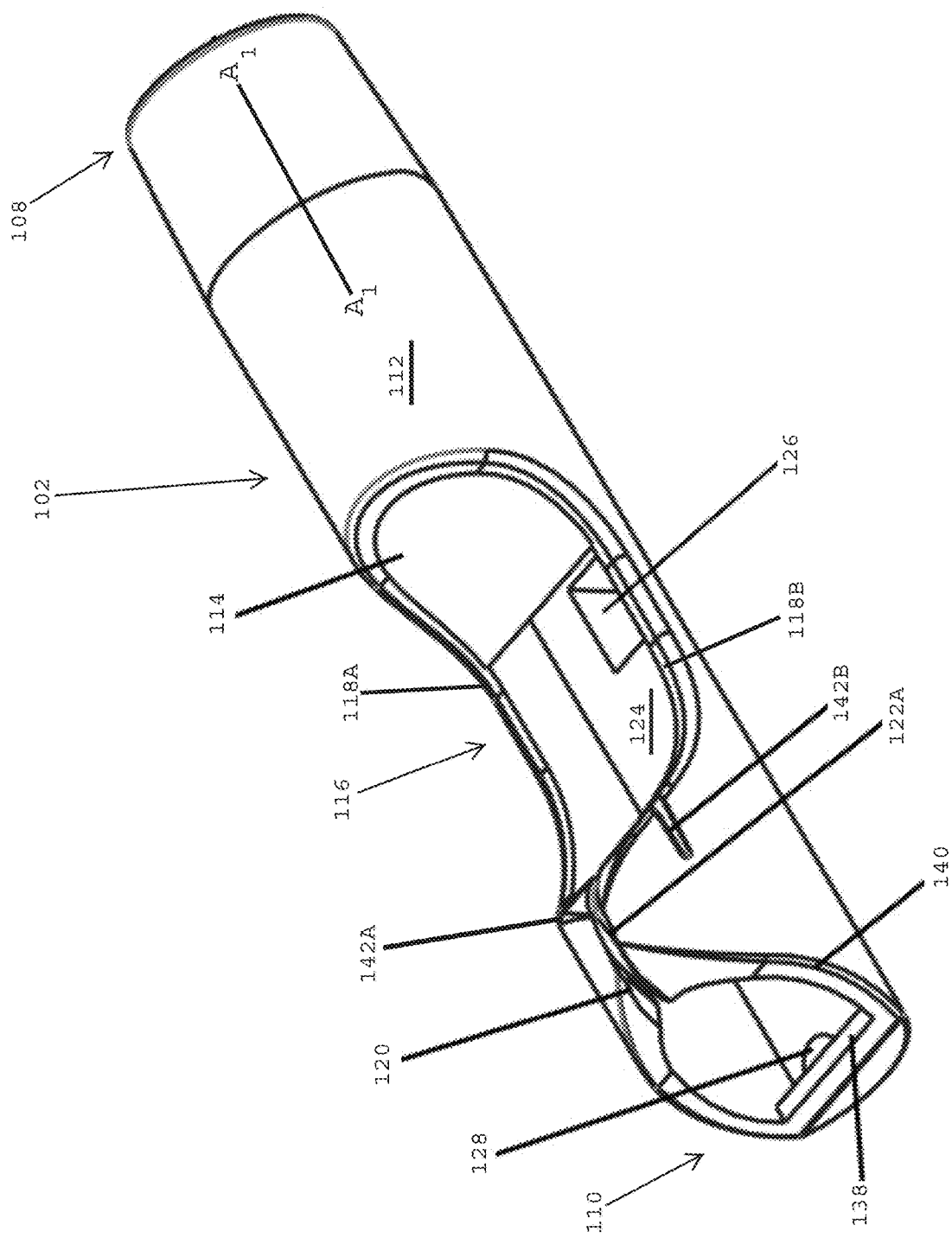
FIG. 2A is a perspective view of a top side of the needle camera adaptor shown in FIGS. 1A and 1B.
Figure 2B:
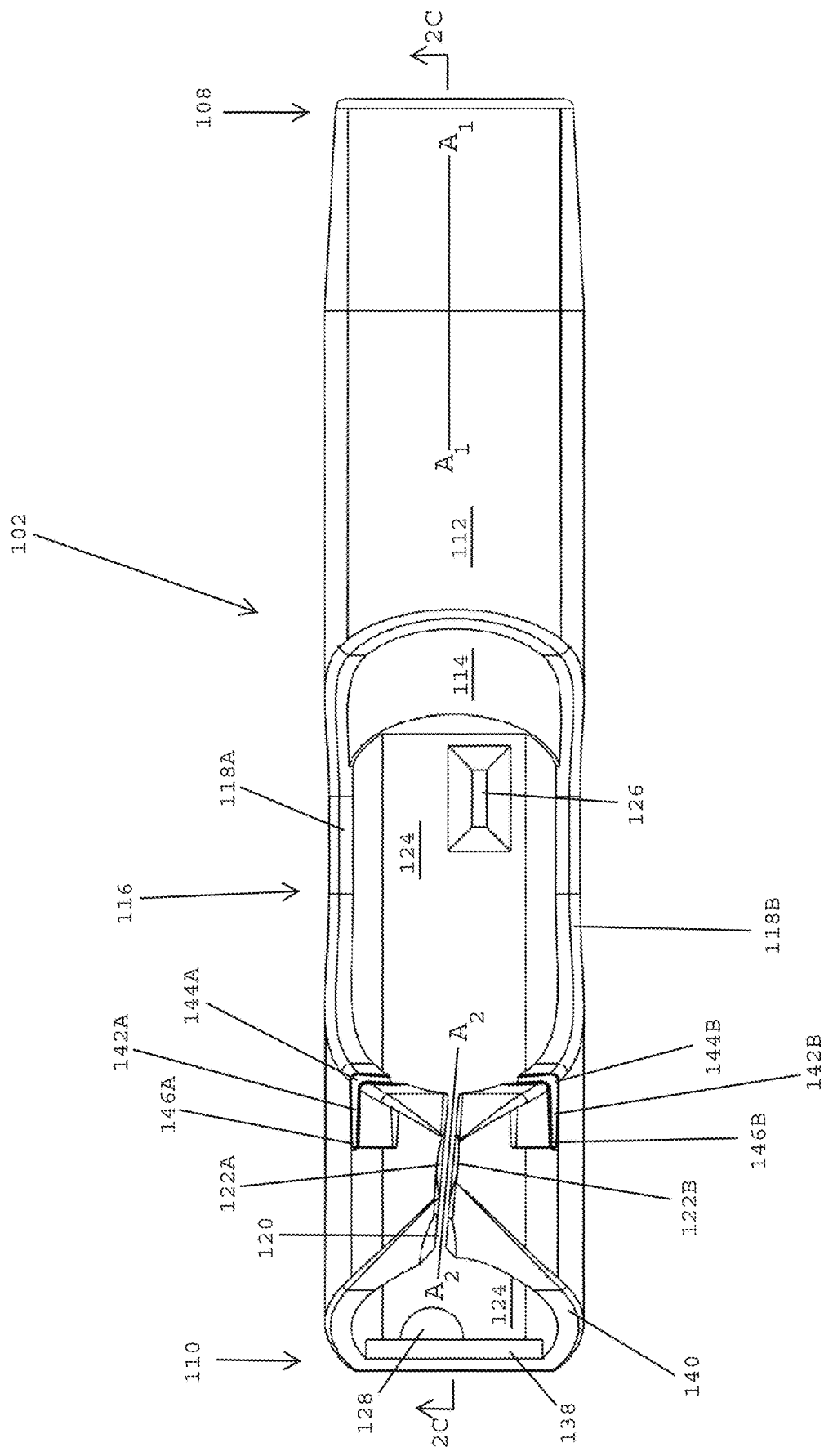
FIG. 2B is a top plan view of the needle camera adaptor shown in FIG. 2A.
Figure 2C:
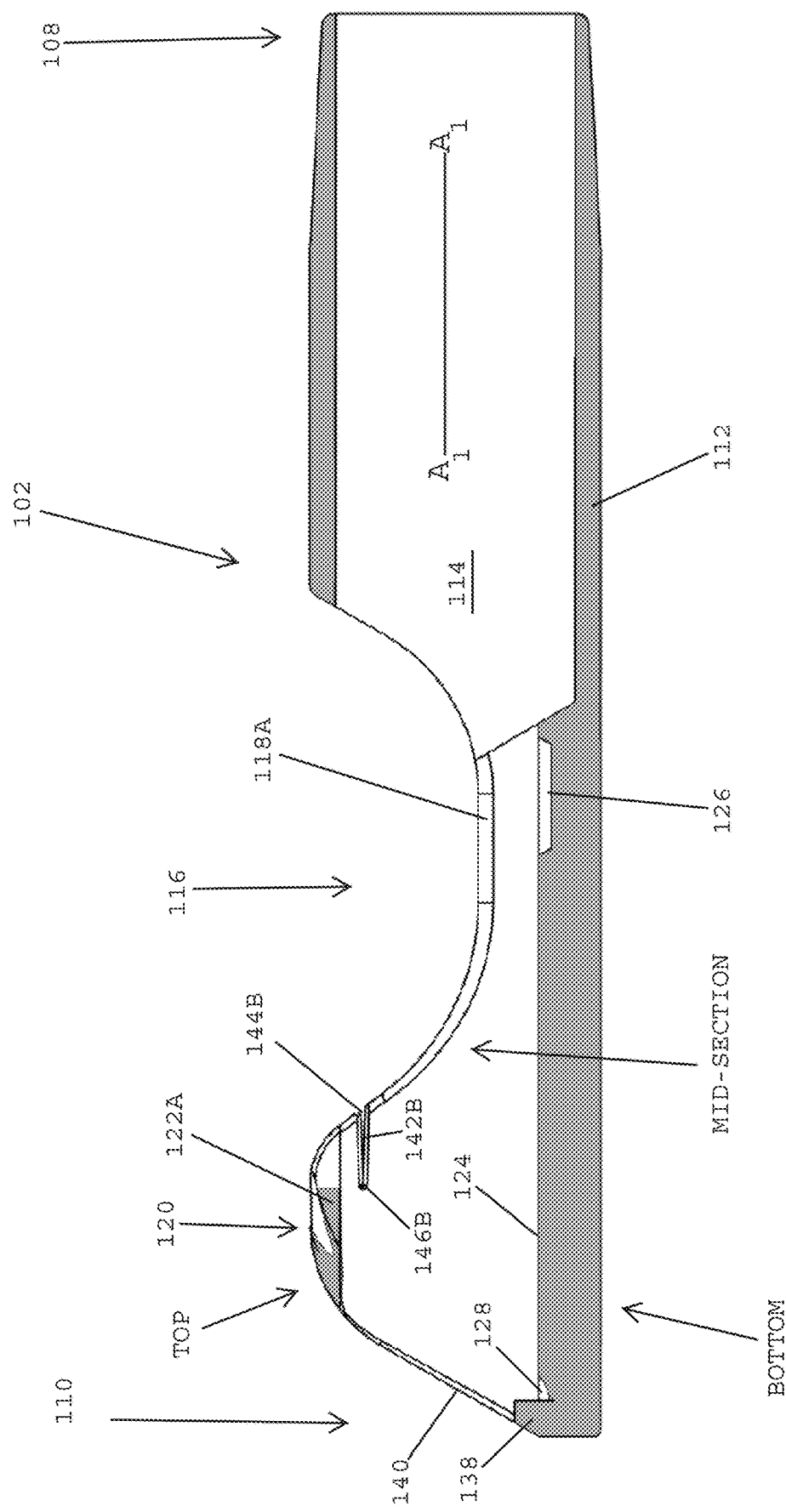
FIG. 2C is a cross-sectional view of the needle camera adaptor shown in FIG. 2B.

Referring to FIGS. 2A-2C, in one embodiment, the needle camera adaptor 102 preferably has a proximal end 108 and a distal end 110. In one embodiment, the needle camera adaptor 102 preferably has an outer wall 112, such as a tube-shaped outer wall, that extends along the length of the needle camera adaptor between the proximal and distal ends 108, 110 thereof. The outer wall 112 may have a generally cylindrical shape and may have a varying thickness. In one embodiment, the needle camera adaptor 102 preferably has a central lumen 114 that extends along a central or longitudinal axis $A_1$ thereof. The lumen 114 preferably extends from the proximal end 108 to the distal end 110 of the needle camera adaptor. The central lumen 114 may be utilized for securing a distal end of the endoscope 106 (FIG. 1A) to the proximal end 108 of the needle camera adaptor 102 and/or for providing visual access to the suture needle 104 as the combination of the needle camera adaptor and the suture needle are delivered through a cannula to a surgical site. The proximal end of the central lumen 114 may include a fully circular bore or may include flats, ribs or other non-circular geometries to facilitate proper alignment and/or a secure engagement between the distal end of the surgical endoscope 106 (FIGS. 1A and 1B) and the proximal end 108 of the needle camera adaptor 102.

In one embodiment, the needle camera adaptor 102 preferably has a central region 116 that is open and that is defined by lateral edges 118A, 118B having a skived profile. In one embodiment, the central region 116 defines a lower lateral profile region of the needle camera adaptor, which enables a surgical instrument (e.g., a needle driver) to be inserted into the central region for removing a suture needle from its attachment with the needle camera adaptor. The opening in the central region may be referred to as a lateral access opening or an external access opening that enables a surgical tool to be inserted into the central region for releasing and/or removing a curved suture needle from its attachment to the needle camera adaptor.

In one embodiment, the needle camera adaptor 102 desirably includes a needle securing channel 120 formed in a topside of the tube-shaped outer wall 112 of the needle camera adaptor. In one embodiment, the needle securing channel 120 preferably extends between the distal end of the central region 116 and the distal end 110 of the needle camera adaptor. In one embodiment, the needle securing channel 120 is adapted to receive and hold a suture needle such as an armed suture needle. In one embodiment, the needle camera adaptor 102 preferably includes opposing resilient elements 122A, 122B (e.g., scalloped features) that are located on opposite sides of the needle securing channel 120, which may apply compressive forces on lateral sides of the suture needle for holding the suture needle within the needle securing channel 120. In one embodiment, a gap between the opposing resilient elements 122A, 122B is preferably slightly smaller than the width of the needle securing channel 120. In one embodiment, the suture needle is releasably secured within the needle securing channel 120.

In one embodiment, the needle camera adaptor 102 preferably has a floor 124 or inner surface that extends through the central region 116 and toward the distal end 110 of the needle camera adaptor. In one embodiment, the needle camera adaptor 102 desirably includes a suture relief pocket 126, also known as a proximal needle securing recess, which is formed in the floor 124 within the central region 116 of the needle camera adaptor. As will be described in more detail herein, the suture relief pocket 126 (a/k/a proximal needle securing recess) is adapted to seat a proximal end of a suture needle and a portion of a suture strand that is secured to the proximal end of the suture needle.

In one embodiment, the suture relief pocket 126 is offset from the longitudinal or central axis $A_1$ of the needle camera adaptor 102 and provides a locating feature for the proximal end of a suture needle having an attached suture thread.

In one embodiment, the needle camera adaptor 102 desirably includes a needle point recess 128, also known as a distal needle securing recess, which is formed in the floor 124 or inner surface of the tube-shaped body and that is located adjacent the distal end 110 of the needle camera adaptor 102. The needle point recess 128 (a/k/a the distal needle securing recess) is adapted to receive and seat the sharpened pointed tip of a suture needle (e.g., a curved surgical needle) to prevent the sharpened pointed tip from scratching the inner surface of a cannula and/or contacting a patient's tissue as the suture needle is passed through a cannula for being positioned at a surgical site.

In one embodiment, the needle camera adaptor 102 preferably has a distal end wall 138 or distal stop that extends laterally across the distal end 110 of the needle camera adaptor and along a lower end of the needle camera adaptor 102. The distal end wall 138 preferably projects slightly above the floor 124 or inner surface of the needle camera adaptor 102 and desirably functions as a stop to prevent the sharpened tip of a curved surgical needle from extending beyond the distal end 110 of the needle camera adaptor 102, which prevents the point from being damaged and/or from scratching the cannula during passage through the cannula.

In one embodiment, the distal end 110 of the needle camera adaptor 102 preferably includes a sloping distal end face 140 that defines an oblique angle at the distal end 110 of the needle camera adaptor 102. The oblique angle of the sloping distal end face 140 preferably facilitates passing the needle camera adaptor 102 through a cannula, or through a seal at a proximal end of a trocar.

In one embodiment, the needle camera adaptor 102 preferably includes a pair of suture retrieval slots 142A, 142B that are formed in the outer wall 112 of the needle camera adaptor 102. In one embodiment, the pair of suture retrieval slots 142A, 142B are adapted to seat a suture strand for removing the suture needle and the suture strand from a surgical site. At the end of a surgical procedure, when it is desired to remove the suture needle and the suture thread from a patient, the suture is preferably inserted and/or pressed into the suture retrieval slots 142A, 142B.

Referring to FIG. 2B, in one embodiment, the needle securing channel 120 is formed with two opposing resilient elements 122A, 122B, which may include two semi-circular features on the channel 120. In this configuration, the opposing resilient elements 122A, 122B result in a portion of the needle securing channel 120, located near the central region of the needle securing channel 120, that is greater in width than the abutting regions and is suited to receive the elongated body portion of the suture needle 104 (FIG. 1A).

Referring to FIG. 2B, in one embodiment, the needle camera adaptor 102 preferably has a length that extends along a central or longitudinal axis $A_1$ thereof between the proximal end 108 and the distal end 110. In one embodiment, the needle securing channel 120 is adapted to engage the sides of a suture needle when the suture needle is secured to the needle camera adaptor 102. In one embodiment, the needle securing channel 120 preferably extends along a second axis $A_2$ that defines an oblique angle relative to the longitudinal axis $A_1$. Thus, a suture needle may be mounted to the needle camera adaptor 102 at a slightly skewed orientation relative to the longitudinal axis $A_1$ of the needle camera adaptor. The skewed orientation of the suture needle desirably enables the suture needle, and particularly the side of the suture needle, to be continuously viewed on a video monitor as the suture needle is passed through a cannula and delivered to a surgical site.

The continuous visualization feature is important because the endoscopic lens and associated views may not be movable relative to the curved suture needle. The ability to visualize the side of the curved suture needle, due to the slightly skewed orientation along the second axis $A_2$, preferably facilitates grasping the curved suture needle with a surgical instrument, such as a needle driver. In one embodiment, when grasping the curved suture needle with a surgical instrument, the focal point of an endoscope may be adjusted to near field positioning to enable the visualization during grasping of the suture needle by the needle driver. Once the curved surgical needle is removed from the needle camera adaptor 102, the focal point of the endoscope may be adjusted to a far field setting so that the features of the needle camera adaptor (e.g., outer wall 112) are out of the width of the field of view and do not obstruct the endoscope views.

Referring to FIGS. 2B and 2C, in one embodiment, the suture retrieval slots 142A, 142B of the needle camera adaptor 102 preferably have respective open ends 144A, 144B that face toward the proximal end 108 of the needle camera adaptor, and respective closed ends 146A, 146B that are narrower than the respective open ends. As such, the respective suture retrieval slots 142A, 142B are wider at the open ends 144A, 144B and narrower at the closed ends 146A, 146B thereof.

Referring to FIG. 2C, in one embodiment, the tube-shaped outer wall 112 of the needle camera adaptor 102 preferably has a top side (designated "TOP" in FIG. 2C), a bottom side (designated "BOTTOM" in FIG. 2C), and a mid-section that is located between the top side and the bottom side. In one embodiment, the suture retrieval slots 142A, 142B are preferably located between the mid-section and the top side of the tube-shaped outer wall 112, and more preferably adjacent the top side of the tube-shaped outer wall 112. Positioning the suture retrieval slots 142A, 142B adjacent the top side of the tube-shaped outer wall 112, as well as proper shaping of the suture retrieval slots, desirably minimizes the likelihood that the suture retrieval slots will snag and/or get hung up on the seal flaps of the cannula during removal of the needle camera adaptor 102 and the suture needle from the cannula.

Figure 3:
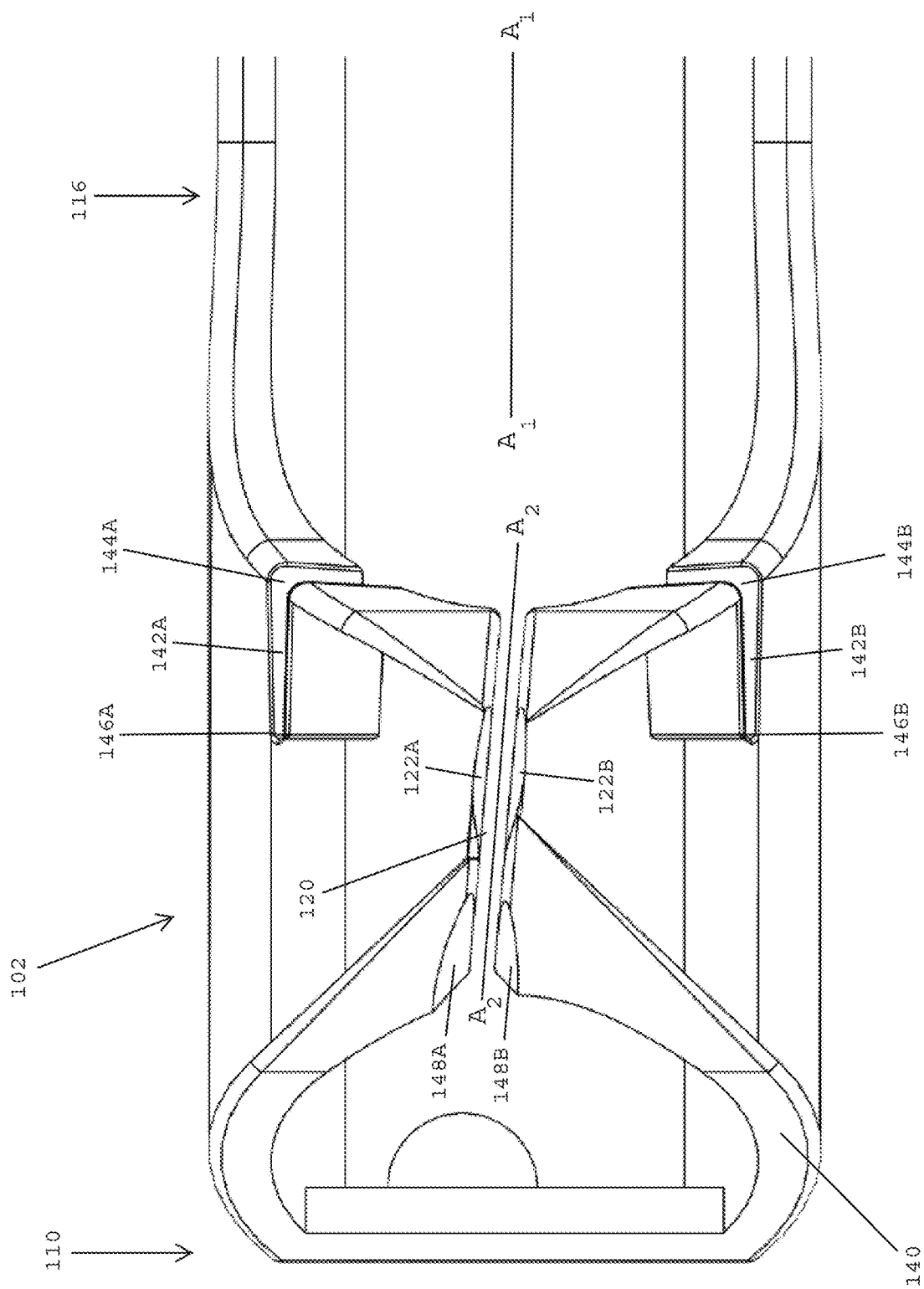
FIG. 3 is a magnified view of the distal end of the needle camera adaptor shown in FIG. 2B.

Referring to FIG. 3, in one embodiment, the needle camera adaptor 102 preferably includes the needle securing channel 120 that extends along a second axis $A_2$ that is skewed relative to the longitudinal axis $A_1$ of the needle camera adaptor. In one embodiment, the needle securing channel 120 preferably extends from a distal end of the central region 116 of the needle camera adaptor 102 to the sloping distal end face 140 that is adjacent the distal end 110 of the needle camera adaptor 102.

In one embodiment, the needle camera adaptor 102 preferably includes opposing resilient elements 122A, 122B (e.g., scalloped features) that project into opposing sides of the needle securing channel 120 for providing resilient and/or flexible holding elements that are adapted to engage the sides of a suture needle for releasably securing the suture needle within the needle securing channel. In one embodiment, when a suture needle is secured within the channel 120, the opposing resilient elements 122A, 122B preferably apply a light compressive force into the lateral sides of a curved surgical needle for securing the needle to the needle camera adaptor. A surgical instrument may be used for overcoming the compressive forces applied by the opposing resilient elements 122A, 122B so that the suture needle may be removed from the needle camera adaptor for being used during a surgical procedure.

In one embodiment, the needle securing channel 120 is formed at the upper end of the outer wall 112 of the needle camera adaptor 102 and extends between the central region 116 and the sloping distal face 140 of the needle camera adaptor. The wall thickness adjacent the needle securing channel may be thinner to provide a more flexible region of the tube-shaped outer wall.

In one embodiment, the distal end of the surgical needle channel 120 preferably includes opposing guide surfaces 148A, 148B that assist in guiding the elongated body of the curved suture needle into the needle securing channel 120 for releasably securing the suture needle to the needle camera adaptor.

In one embodiment, the distal end of the needle securing channel 120 preferably includes opposing tapered guide surfaces 148A, 148B (adjacent the sloping distal surface 140) that may be used for guiding the curved elongated body of the suture needle into the needle securing channel 120.

In one embodiment, a needle camera adaptor may have one or more suture retrieval slots (e.g., two suture retrieval slots) that are adapted to engage a suture strand.

Figure 4A:
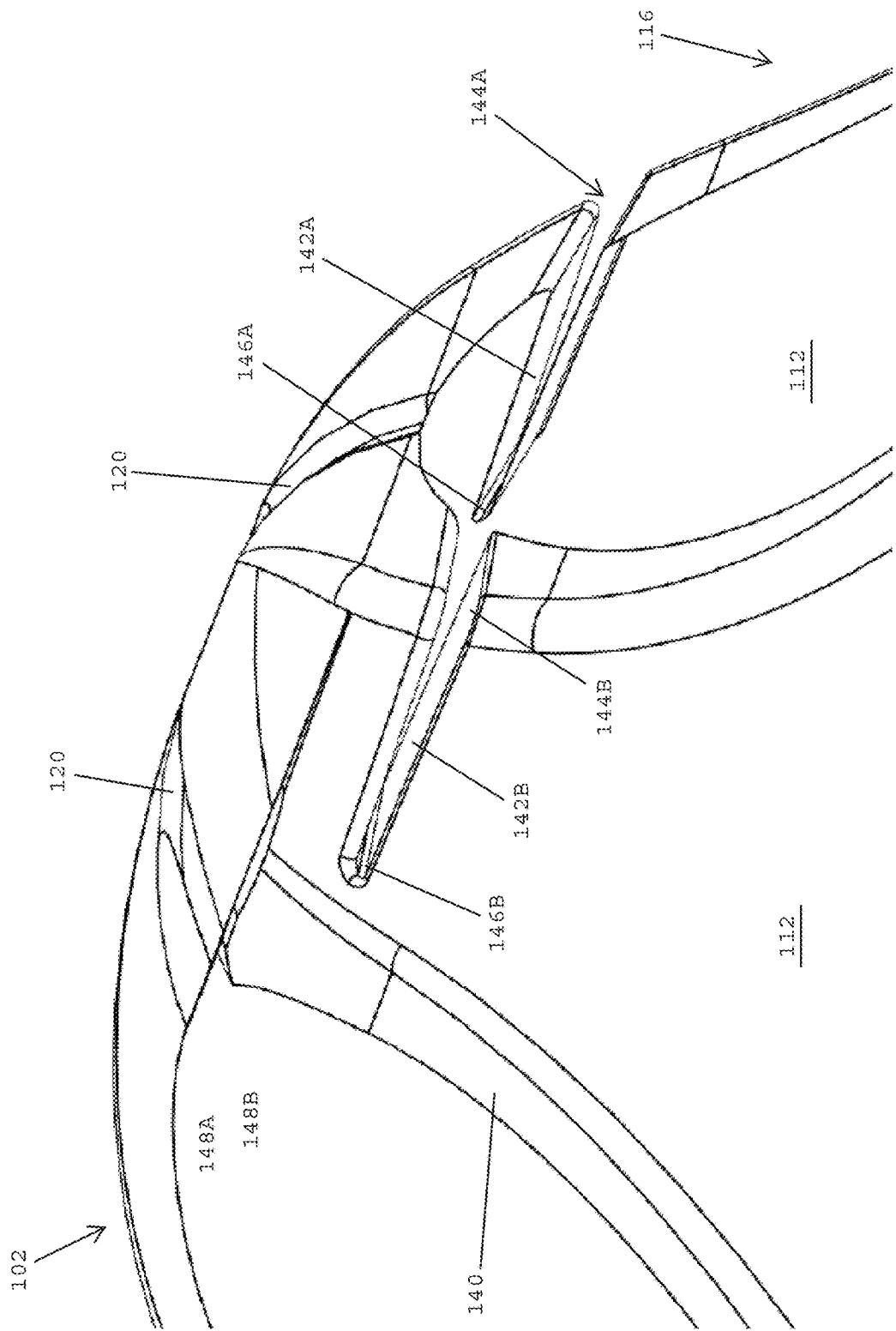
FIG. 4A is a perspective view of a wall of the needle camera adaptor shown in FIG. 3 including a needle securing channel and a pair of suture retrieval slots, in accordance with one embodiment of the present patent application.
Figure 4B:
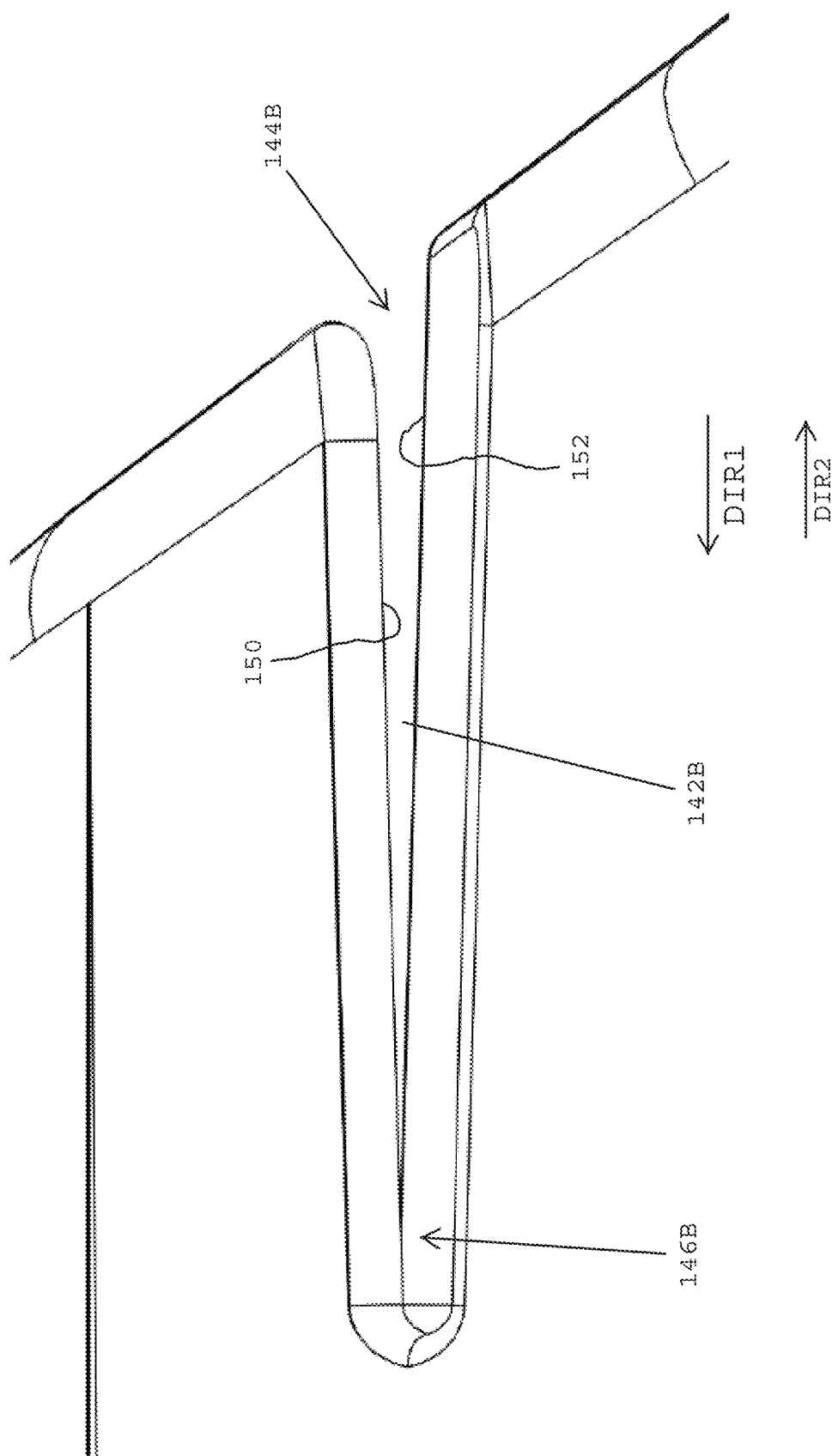
FIG. 4B is a magnified view of a suture retrieval slot shown in FIG. 4A.

Referring to FIGS. 4A and 4B, in one embodiment, the needle camera adaptor 102 preferably includes the pair of suture retrieval slots 142A, 142B that are formed in the outer wall 112 thereof. The first suture retrieval slot 142A desirably has an open end 144A and a closed end 146A. The open end 144A is preferably wider than the closed end 146A so that the suture retrieval slot 142A becomes narrower between the open end 144A and the closed end 146A.

In one embodiment, the second suture retrieval slot 142B has an open end 144B and a closed end 146B. The second suture retrieval slot 142B preferably becomes narrower between the open end 142B and the closed end 146B thereof.

Referring to FIG. 4B, in one embodiment, a suture strand may be inserted into the open end 144B of the second suture retrieval slot 142B and advanced in the distal direction designated DIR1 until the opposing top and bottom surfaces 150, 152 of the second suture retrieval slot 142B engage the outer surface of the suture strand for forming a friction fit between the suture strand and the second suture retrieval slot 142B. After the suture strand has been captured within the second suture retrieval slot 142B, the needle camera adaptor may be retracted in the direction designated DIR2 for retracting the suture strand (and the attached suture needle) through a cannula (e.g., a trocar). A similar friction fit may be formed between the suture strand and the first suture retrieval slot 142A (FIG. 4A).

Figure 5:
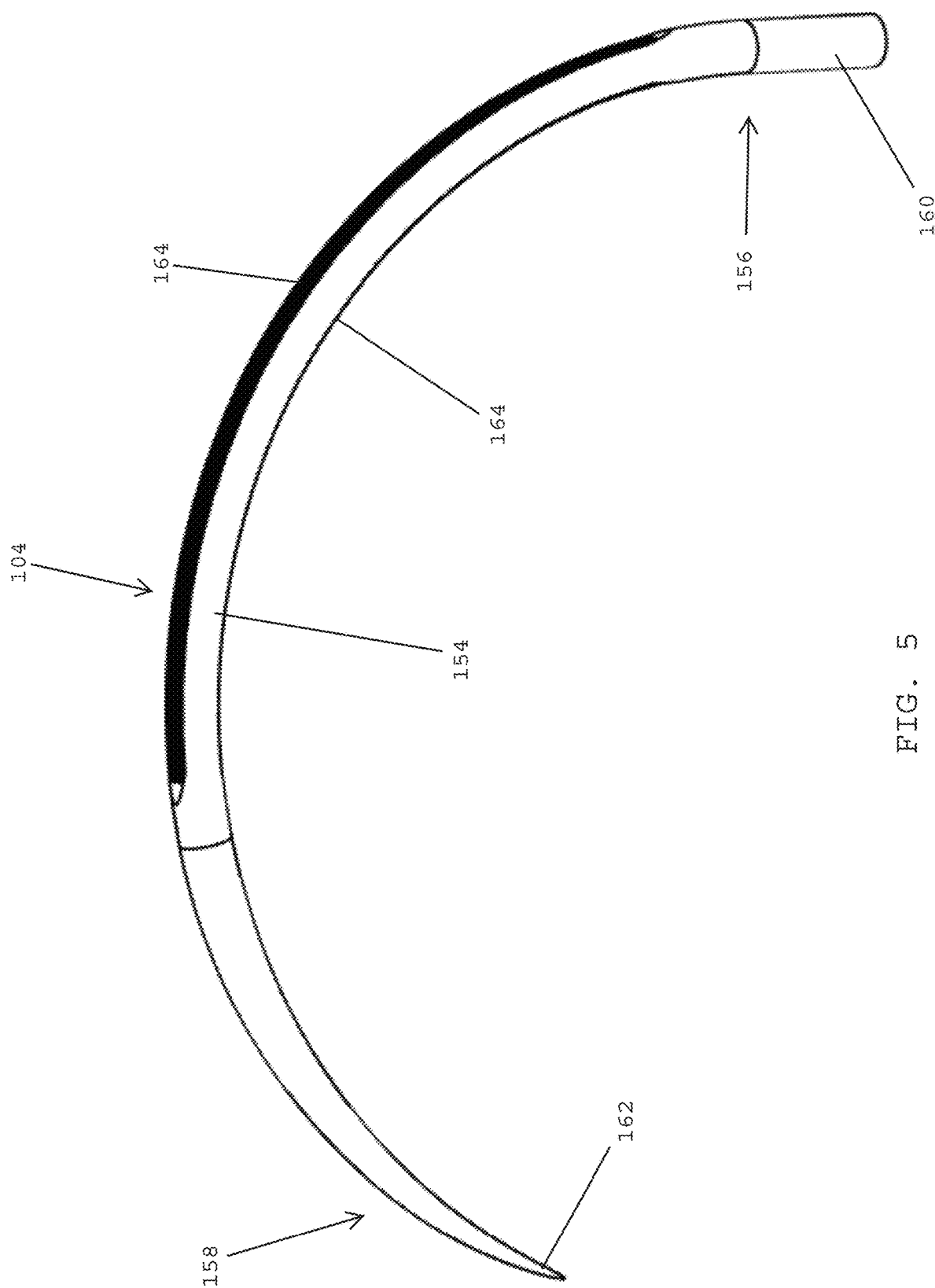
FIG. 5 is a perspective view of a curved surgical suture needle that is adapted to be secured to the needle camera adaptor shown in FIGS. 2A-2C, in accordance with one embodiment of the present patent application.

Referring to FIG. 5, in one embodiment, a suture needle 104, such as a curved surgical needle, may be releasably secured to the needle camera adaptor 102 (FIG. 1A) disclosed herein. In one embodiment, the suture needle 104 may be made of metal such as stainless steel. In one embodiment, the suture needle 104 may be a CT-1 needle sold by Ethicon, Inc. of Somerville, New Jersey. In one embodiment, the suture needle 104 preferably includes a curved elongated body 154 having a proximal end 156 and a distal end 158. In one embodiment, the curved suture needle 104 preferably includes a suture attachment barrel 160 located at the proximal end 156 of the needle, which is adapted to be secured to a distal end of a suture strand. In one embodiment, the curved suture needle 104 preferably includes a sharpened tip 162 that is adapted to pierce tissue and/or facilitate passage of the curved suture needle 104 through tissue. In one embodiment, the curved suture needle 104 may include a series of elongated grooves 164, knurling, or roughening formed in the outer surface of the elongated body 154 for enabling the curved suture needle 104 to be grabbed or gripped by a surgical instrument, such as the jaws of a needle driver. In one embodiment, the elongated grooves 164 preferably extend along the longitudinal axis of the curved elongated body 154 of the suture needle 104.

Referring to FIG. 6A-6C, in one embodiment, the suture needle 104 may be releasably secured to the needle camera adaptor 102. In one embodiment, the elongated body 154 of the suture needle 104 may be pressed into the needle securing channel 120 of the needle camera adaptor 102 so that the suture attachment barrel 160 of the suture needle 104 (and a segment of a suture strand) is disposed within the proximal needle securing recess 126 and the sharpened distal tip 162 of the suture needle 104 is disposed within the distal needle securing recess 128 of the needle camera adaptor 102. In one embodiment, a portion of the needle body 154 preferably passes through the opposing resilient elements 122A, 122B (FIG. 3), which desirably generates a slight compression force on the lateral sides of the needle body to hold the suture needle in place and prevent the accidental release of the suture needle from the needle camera adaptor.

Figure 7:
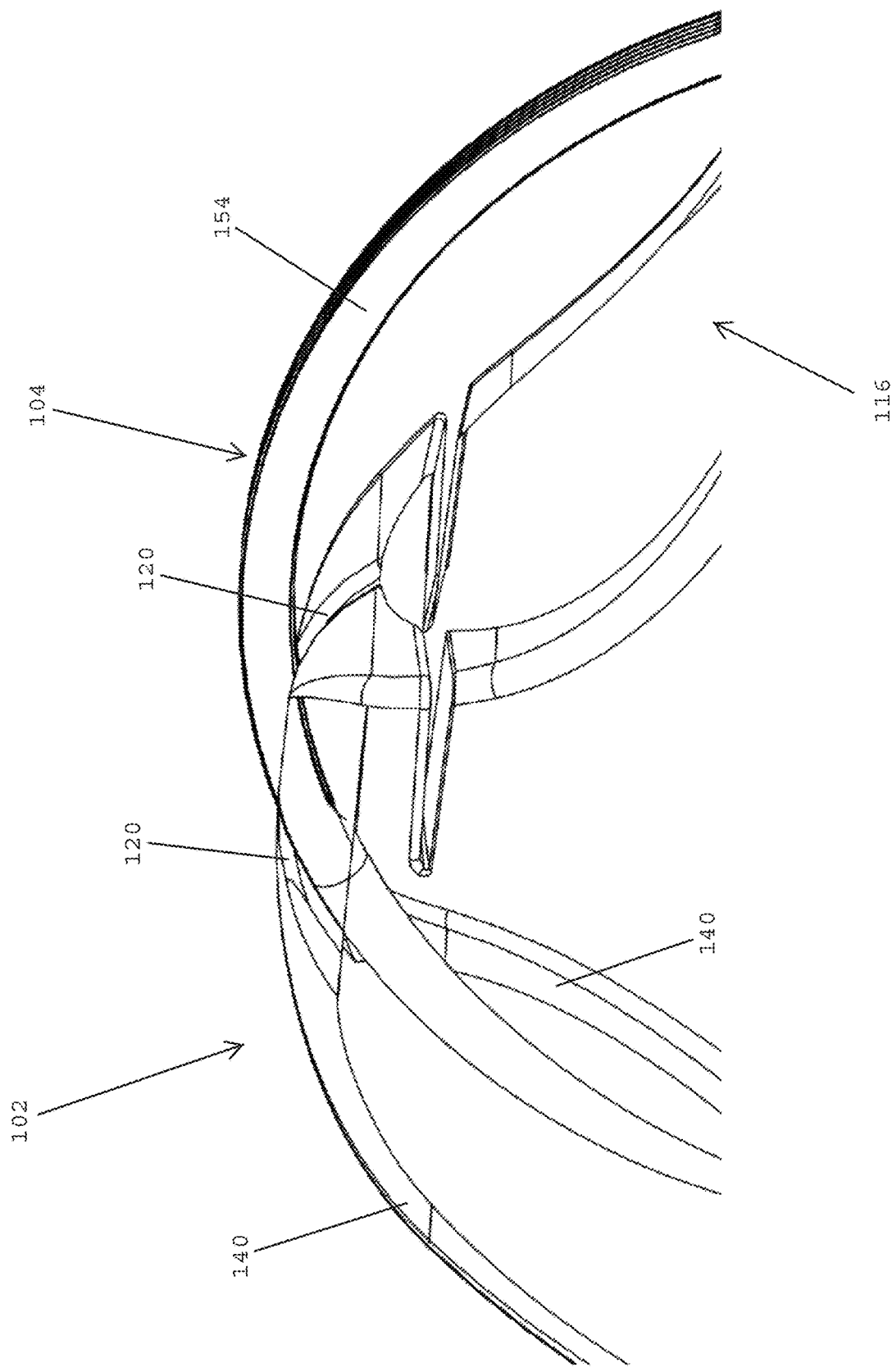
FIG. 7 is a magnified view of a needle securing channel of the needle camera adaptor shown in FIGS. 6A-6C with the curved surgical needle passing through the needle securing channel, in accordance with one embodiment of the present patent application.

Referring to FIG. 7, in one embodiment, the suture needle 104 is preferably releasably secured to the needle camera adaptor 102 by pressing the elongated body 154 of the suture needle 104 into the needle securing channel 120 that extends between the central region 116 and the sloping distal face 140 of the needle camera adaptor 102. The needle securing channel 120 preferably includes the afore-mentioned opposing resilient elements 122A, 122B (FIG. 3) that apply a compressive force to the respective lateral sides of the elongated body 154 of the suture needle 104 for releasably securing the suture needle 104 within the needle securing channel 120. The holding force provided by the opposing resilient elements 122A, 122B may be desirably overcome by using a surgical instrument, such as a needle driver, for removing the suture needle 104 from the needle securing channel 120.

Figure 8B:
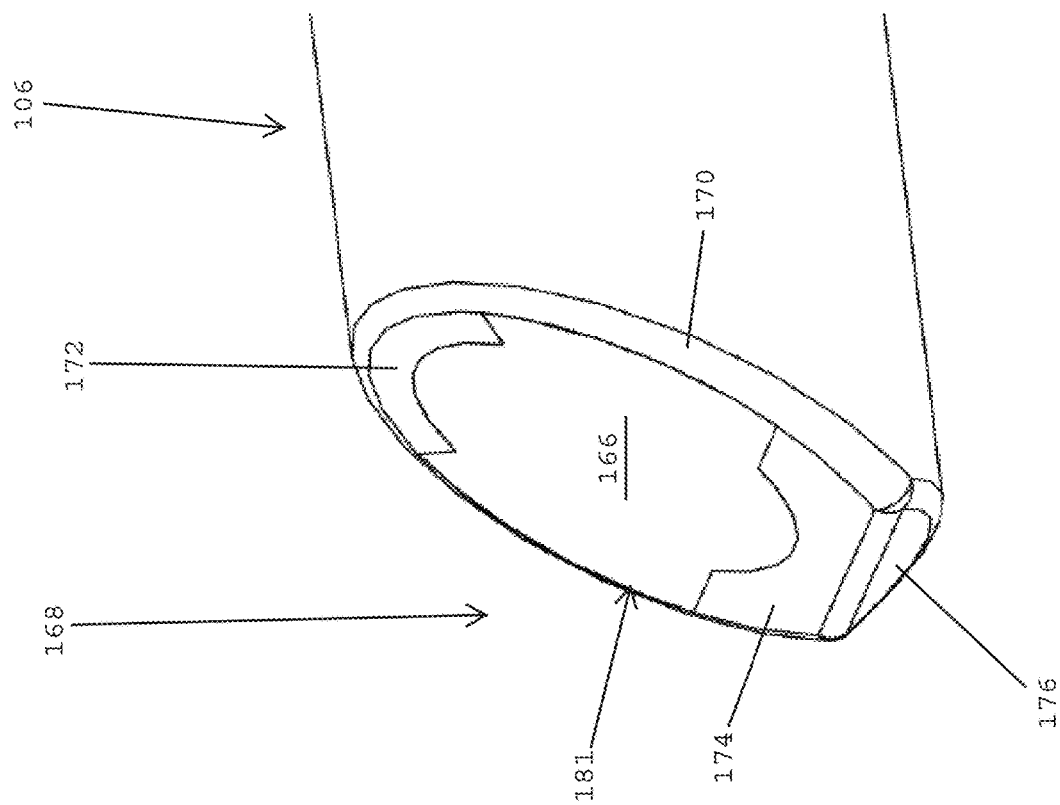
FIG. 8B is another perspective view of the distal end of the endoscope shown in FIGS. 1A, 1B, and 8A.
Figure 8A:
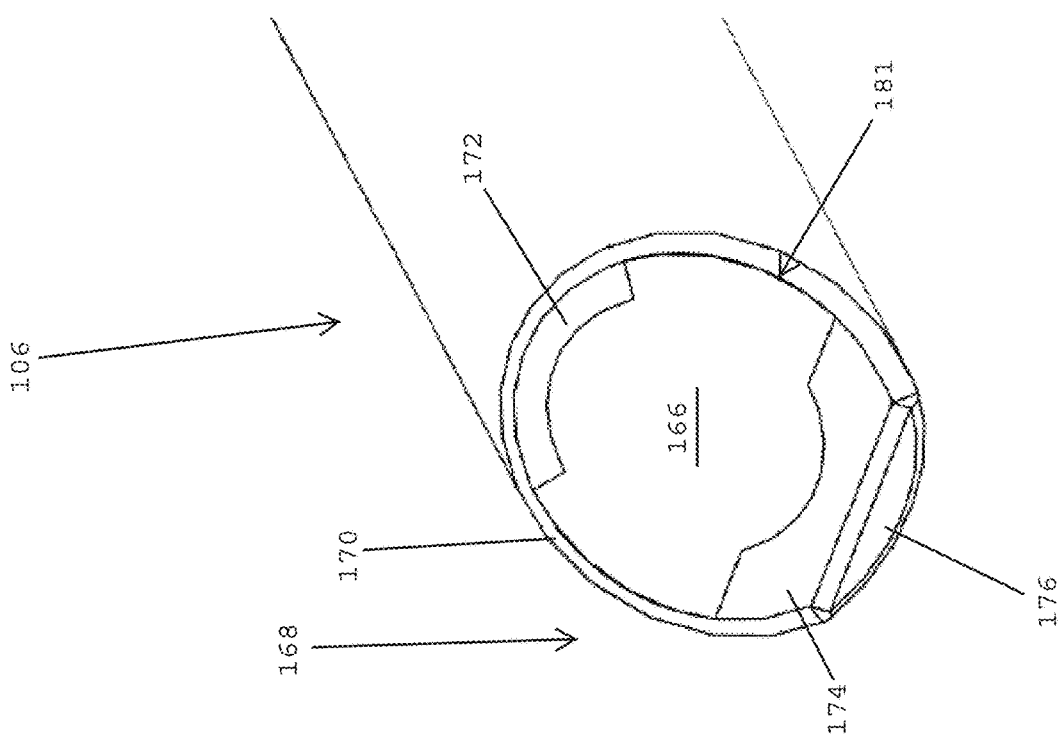
FIG. 8A is a perspective view of a distal end of the endoscope shown in FIGS. 1A and 1B.

Referring to FIGS. 8A and 8B, in one embodiment, the endoscope 106 may include a cannula that desirably has an elongated conduit 166 that extends along the length thereof from a proximal end to a distal end 168 of the endoscope. In one embodiment, the distal end 168 of the endoscope 106 preferably includes a first light element 172 that is located at an upper end of the distal end 168 of the endoscope 106, and a second light element 174 that is located at an underside or lower end of the distal end 168 of the endoscope 106. In one embodiment, each of the first and second light elements 172, 174 may includes one or more fiber optic lights (e.g., bundles of optical fibers) that transmit light for providing visible light at a surgical site. In one embodiment, the first light element 172 may include a first bundle of optical fibers that are designed to provide light at the distal end 168 of the endoscope for illuminating a surgical site. In one embodiment, the second light element 174 may include a second bundle of optical fibers that are also designed to provide light at the distal end 168 of the endoscope for illuminating the surgical site. In one embodiment, the first and second light elements 172, 174 may include light emitting diodes (LEDs).

In one embodiment the opening at the distal end 168 of the endoscope 106 is preferably covered by an optical lens 181 that closes the distal end of the endoscope. The optical lens 181 preferably covers the first and second light elements 172, 174. In one embodiment, the light transmitted from the first and second light elements 172, 174 preferably passes through the optical lens 181 for illuminating a surgical site.

In one embodiment, the distal end 168 of the endoscope 106 preferably includes a stop 176 that extends laterally across the distal end of the endoscope 106, at the lower end or underside of the endoscope, for aligning and orienting the distal end 168 of the endoscope 106 relative to the needle camera adaptor 102 (FIGS. 6A-6C).

In one embodiment, the endoscope 106 may include a camera that is adapted to record moving or still pictures at the distal end 168 of the endoscope 106. In one embodiment, the camera may include its own light source for providing visible light at the distal end 168 of the endoscope 106 and/or at a surgical site.

The endoscope 106 shown and described above merely discloses one design for an endoscope, telescope and/or visualization device that may be assembled with a needle camera adaptor, and is not intended to limit the scope of various types of devices that may be utilized. For example, in one embodiment, an endoscope that may be assembled with one of the needle camera adaptors disclosed herein may include one or more of the telescopes or visualization devices sold under the trademark HOPKINS® by Karl Storz SE & Co. KG of Tuttlingen, Germany (hereinafter referred to as Karl Storz). In one embodiment, an endoscope configured for being assembled with one of the needle camera adaptors disclosed herein may be Model #26003 AA (10 mm diameter), sold under the trademark HOPKINS® Straight Forward Telescope 0° by Karl Storz. In one embodiment, an endoscope configured for being assembled with one of the needle camera adaptors disclosed herein may be Model #26003 BA (10 mm diameter), sold under the trademark HOPKINS® Forward-Oblique Telescope 30° by Karl Storz.

Referring to FIG. 9A, in one embodiment, the needle camera adaptor 102 has the proximal end 108 and the central lumen 114 that extends along the longitudinal axis $A_1$ of the needle camera adaptor 102. In one embodiment, the needle camera adaptor 102 preferably includes a stop surface 178 (e.g., a sloping surface) that extends laterally across the width of the needle camera adaptor and that faces toward the proximal end 108 of the needle camera adaptor.

Referring to FIGS. 9A and 9B, in one embodiment, the needle camera adaptor 102 may be assembled with the endoscope 106 by directing the sloping distal face 170 at the distal end 168 of the endoscope 102 into the proximal opening at the proximal end 108 of the needle camera adaptor. The distal end 168 of the endoscope 106 is preferably advanced in the distal direction DIR1 until the sloping surface of the stop 176 at the distal end of the endoscope abuts against the stop 178 of the needle camera adaptor 102. The sloping surfaces of the opposing stops 176, 178 are preferably mirror images of one another and preferably have a similar slope. The opposing sloping stops 176, 178 preferably align and orient the needle camera adaptor 102 relative to the distal end 168 of the endoscope 106. The endoscope 106 preferably captures still and/or moving images of the suture needle secured to the needle camera adaptor 102, thereby providing continuous visualization of the suture needle as the needle camera adaptor 102 and the suture needle are delivered through a cannula for being deployed at a surgical site.

In one embodiment, an endoscope and a needle camera adaptor may not have orienting features such as the opposing stops 176, 178 shown and described above in FIGS. 9A and 9B.

Figure 10:
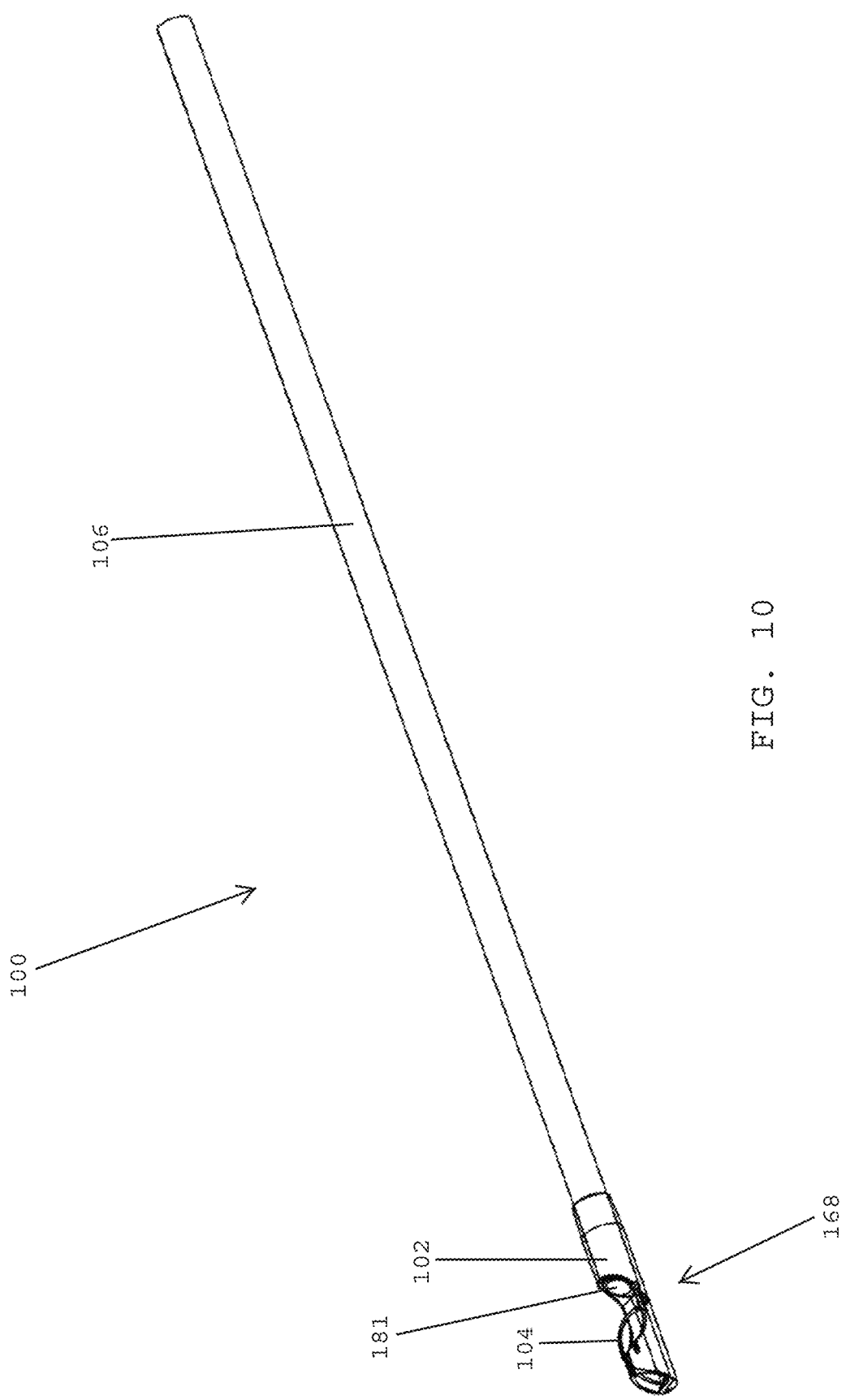
FIG. 10 is a perspective view of the system shown in FIGS. 1A and 1B after the needle camera adaptor has been assembled with the distal end of the endoscope.

FIG. 10 shows the system 100 of FIGS. 1A-9B after the needle camera adaptor 102 has been assembled with the distal end 168 of the endoscope 106. The curved suture needle 104 is releasably secured to the needle camera adaptor 102 so that the curved suture needle may be advanced through a cannula for being positioned at a surgical site. As the curved suture needle 104 is advanced through a cannula to a surgical site, visualization of the curved surgical needle 104 may be maintained at all times via the visualization device, or camera, that is assembled to the proximal end of the endoscope 106.

Figure 11:
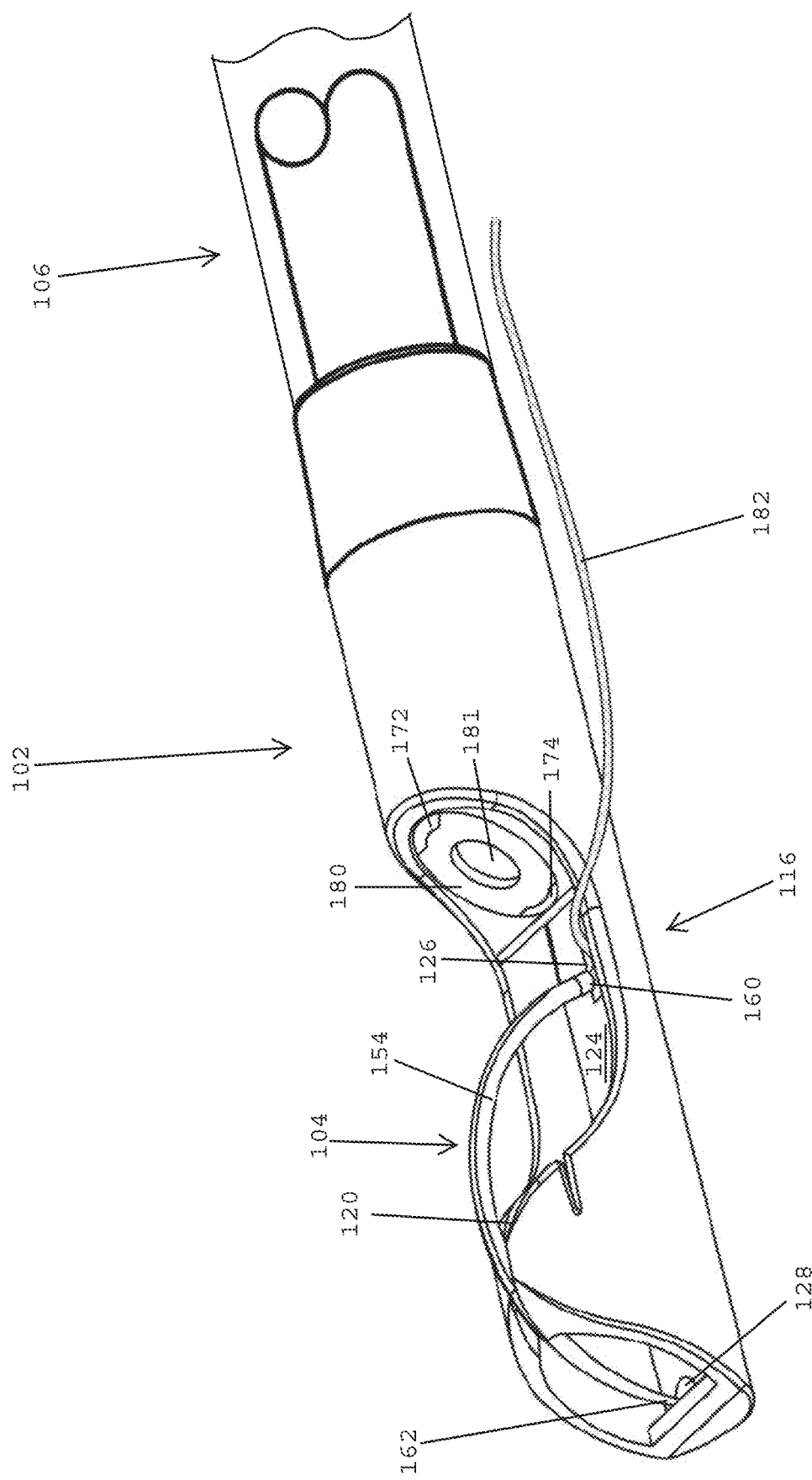
FIG. 11 is a perspective view of a needle camera adaptor having a curved surgical needle secured to the needle camera adaptor and a camera assembled with a proximal end of the needle camera adaptor for visualizing the curved surgical needle as the needle camera adaptor and the curved surgical needle are advanced through a cannula for placement at a surgical site, in accordance with one embodiment of the present patent application.

Referring to FIG. 11, in one embodiment, the needle camera adaptor 102 is secured to the distal end of the endoscope 106, whereupon the system may capture video and/or images of the curved suture needle 104 that is positioned within the central region 116 of the needle camera adaptor 102. The first and second light elements 172, 174 desirably provide light for the visualization device 180 so that video images of the suture needle 104 may be captured by the system. The optical lens 181 of the endoscope 106 is desirably exposed and the focal width is located within the inner lumen of the needle camera adaptor 102. In one embodiment, the visualization device 180 (e.g., a camera), the optical lens 181, and the first and second light elements 172, 174 are all integrated together into the endoscope 106 and function together as a unified component that is assembled with the needle camera adaptor 102.

In one embodiment, the elongated body 154 of the curved suture needle 104 is releasably secured within the needle securing channel 120 of the needle camera adaptor 102. The sharpened tip 162 of the curved suture needle 104 is preferably secured within the distal needle securing recess 128 (e.g., a needle point recess) and the suture attachment barrel 160 is preferably secured within the proximal needle securing recess 126 (e.g., suture relief pocket) formed in the floor 124 or inner surface of a tube-shaped wall of the needle camera adaptor 102. A distal end of a suture thread 182, which is secured to the needle attachment barrel 160, desirably extends from the proximal needle securing recess, through the skived portion, and extends proximally along the external surface of the needle camera adaptor 102.

In one embodiment, the suture needle 104 is mounted in a slightly skewed orientation (i.e., along axis $A_2$ shown in FIG. 2B) relative to the central or longitudinal axis $A_1$ (FIG. 3) of the needle camera adaptor 102. This skewed orientation enables the visualization of the side of the curved suture needle. This feature is important as the endoscope lens 181 and associated view is not movable relative to the suture needle 104. The ability to visualize the side of the suture needle 104 facilitates grasping the suture needle with a surgical instrument, such as a needle driver. In one embodiment, to grasp the suture needle 104, the focal point of the visualization device 180 may be adjusted to near field positioning to enable the visualization during the arming of the needle driver. Once the suture needle 104 is removed by the needle driver from the needle camera adaptor 102, the focal point of the visualization device 180 may be adjusted to a far field setting so that the structural features of the needle camera adaptor 102 are out of the width of the field of view and do not obstruct the views of the visualization device 180.

Figure 12A:
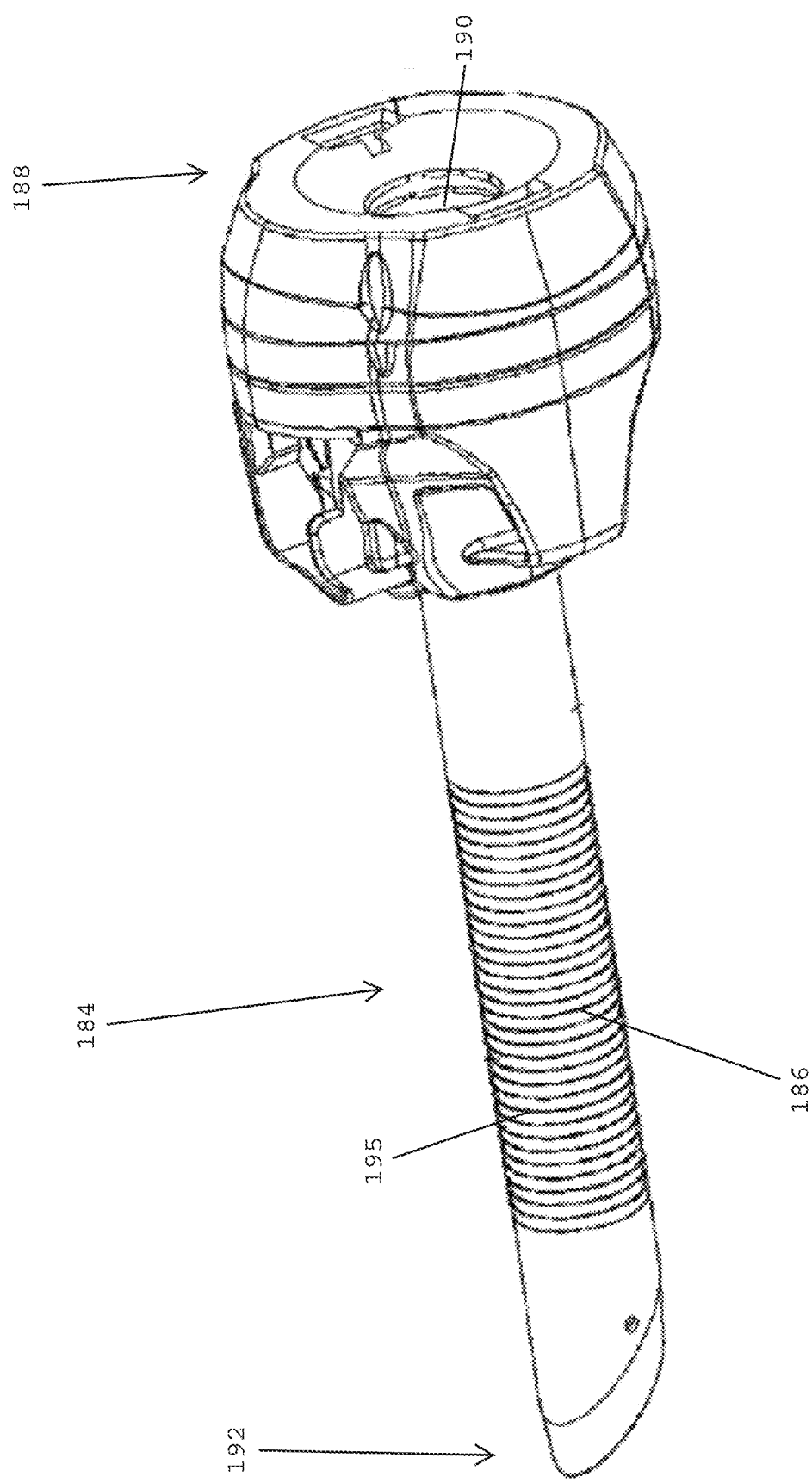
FIG. 12A is a perspective view of a trocar used for delivering the needle camera adaptor and the curved surgical needle of FIG. 11 to a surgical site, in accordance with one embodiment of the present patent application.

Referring to FIG. 12A, in one embodiment, a cannula 184, such as a trocar, may be utilized for advancing the needle camera adaptor 102, the curved suture needle 104 secured thereto (FIG. 11), and the suture strand 182 to a surgical site. The cannula 184 desirably provides percutaneous access to inner regions within the human body. In one embodiment, the cannula 184 desirably has an elongated tube 186 with a proximal end 188 including a seal 190 and a distal end 192. The elongated tube 186 preferably has a conduit that extends between the trocar seal 190 and the distal end 192 thereof.

The elongated tube 186 may be made from metallic and/or polymeric materials. In one embodiment, the elongated tube 186 may be produced with frictional engagement features 195, such as raised rings or ribs. In embodiments in which the elongated tube 186 is made of polymeric materials, the tube may comprise transparent materials to enable the visualization of items disposed inside the tube.

In one embodiment, when the cannula 184 is inserted into a patient for abdominal surgery, the distal end 192 of the elongated tube 186 is exposed to the visceral compartment and the seal 190 is near the patient's skin. The inner lumen of the surgical cannula assembly 184 is accessed through the proximal seal 190 and provides direct access to the visceral compartment for endoscopic instrumentation.

Figure 12B:
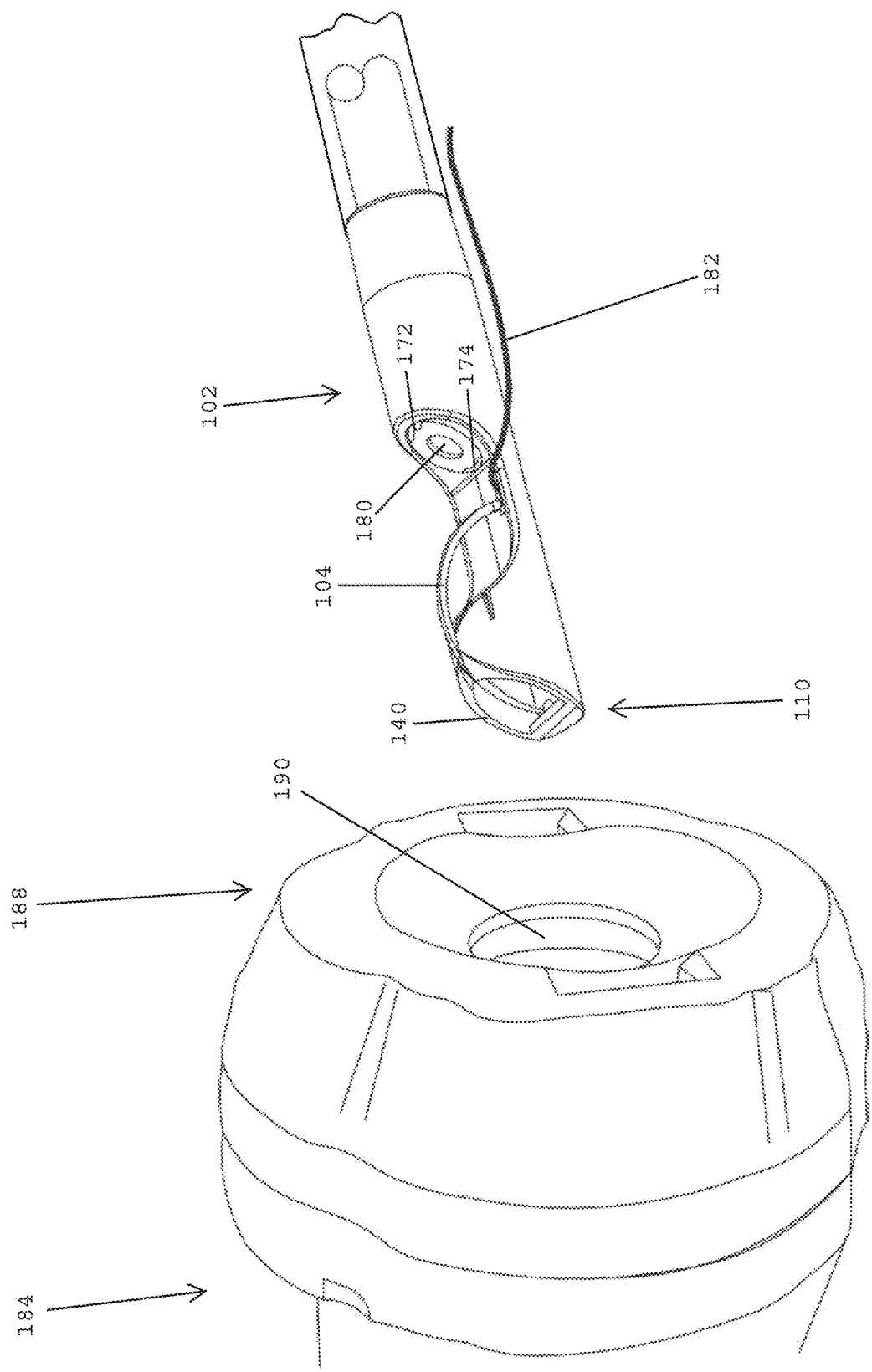
FIG. 12B illustrates a method of inserting the needle camera adaptor and the curved surgical needle secured to the needle camera adaptor into a proximal end of the trocar of FIG. 12A, in accordance with one embodiment of the present patent application.

Referring to FIG. 12B, in one embodiment, the distal end 110 of the needle camera adaptor 102 may be inserted into the proximal end 188 of the cannula 184 by advancing the sloping distal face 140 of the needle camera adaptor through the seal 190 of the cannula 184. In one embodiment, the needle camera adaptor 102, the suture needle 104 and the suture thread 182 may be advanced through the opening at the distal end 192 of the elongated tube 186 of the cannula 184 (FIG. 12A). As the needle camera adaptor 102 is advanced to the distal end of the elongated tube 186 of the cannula 184, the visualization device 180 may be used for simultaneously visualizing the suture needle 104 during passage through the cannula and subsequent placement within an endoscopic surgical site.

In FIG. 12B, the assembly of the needle camera adaptor 102 and the endoscope 106 is shown prior to insertion through the proximal seal ring 188. As can be seen, the suture needle 104 is ideally positioned for insertion through the cannula assembly 184 with the needle tip 162 protected from potential damage while the expansible sealing valve 190 at the proximal end 188 of the cannula 184 is protected from damage during insertion of the suture needle 104. As the needle camera adaptor 102, the suture needle 104, the suture strand 182, and the endoscope 106 are inserted into the cannula 184, the surgical suture strand 182 extends along the side of the needle camera adaptor 102 and the endoscope and out of the expansible sealing valve 190 until it is pulled into the visceral compartment.

Figure 13:
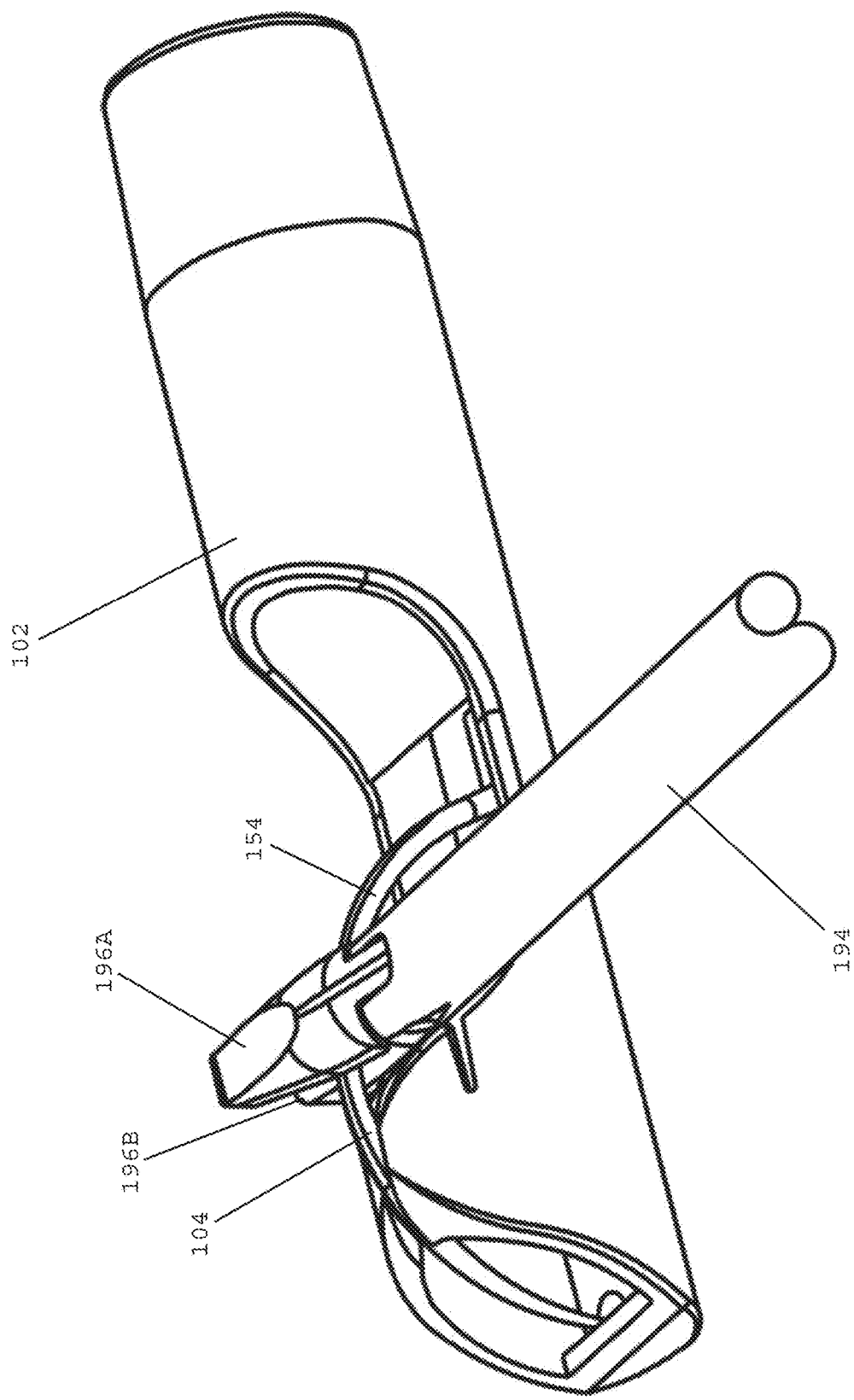
FIG. 13 illustrates a method of using a needle driver for removing the curved surgical needle shown in FIG. 12B from a needle securing channel of the needle camera adaptor, in accordance with one embodiment of the present patent application.

Referring to FIG. 13, after the needle camera adaptor 102 and the curved suture needle 104 have been passed through the cannula 184 (FIGS. 12A and 12B) for being positioned at a surgical site, the curved suture needle 104 is preferably uncoupled and/or removed from its attachment to the needle camera adaptor. In one embodiment, a needle driver 194 having opposing jaws 196A, 196B may be used for grasping the elongated body 154 of the curved suture needle 104 and removing the curved suture needle from the needle securing channel 120 (FIG. 11) of the needle camera adaptor 102. The visualization device 180 (FIG. 11) may be used for visualizing the suture needle 104 and the needle driver 194 as the needle driver is used for removing the suture needle 104 from the needle camera adaptor 102.

Figure 14:
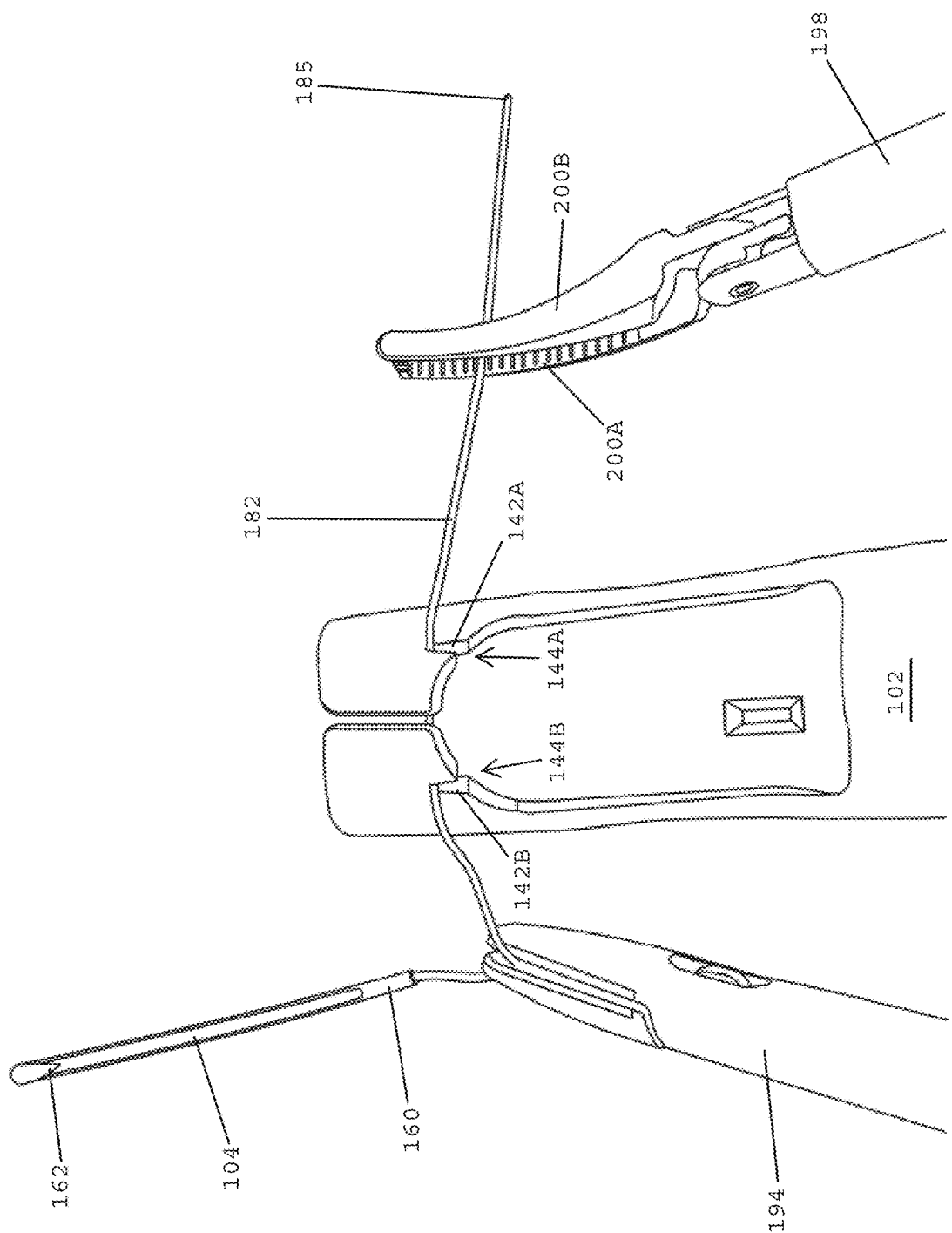
FIG. 14 illustrates a method of positioning a suture strand within suture retrieval slits of a needle camera adaptor, in accordance with one embodiment of the present patent application.

Referring to FIG. 14, in one embodiment, at the conclusion of a surgical procedure, the suture needle 104 and the suture 182 secured thereto are preferably retracted from the surgical site for being removed from a patient. In one embodiment, the suture 182 extends from the needle attachment barrel 160 of the curved suture needle 104. The suture 182 preferably has a free or cut end 185. In one embodiment, the needle driver 194 is utilized to grasp an end of the suture 182 that is adjacent the needle attachment barrel 160 of the curved suture needle 104, and a grasping tool 198 having opposing jaws 200A, 200B is preferably utilized for grasping the suture 182 near the free or cut end 185 of the suture. Tension may be applied to a section of the suture 182 that is located between the needle driver 194 and the grasping tool 198, whereupon the tensioned section of the suture 182 that is located between the instruments 194, 198 may be pushed into the open ends 144A, 144B of the respective suture retrieval slots 142A, 142B. In the position shown in FIG. 14, the suture 182 is secured within the suture retrieval slots 142A, 142B of the needle camera adaptor 102 in preparation for being removed from the surgical site via the cannula 184 (FIGS. 12A and 12B). In one embodiment, the sharpened tip 162 of the curved suture needle 104 is desirably located away from the suture retrieval slots 142A, 142B of the needle camera adaptor 102.

Figure 15:
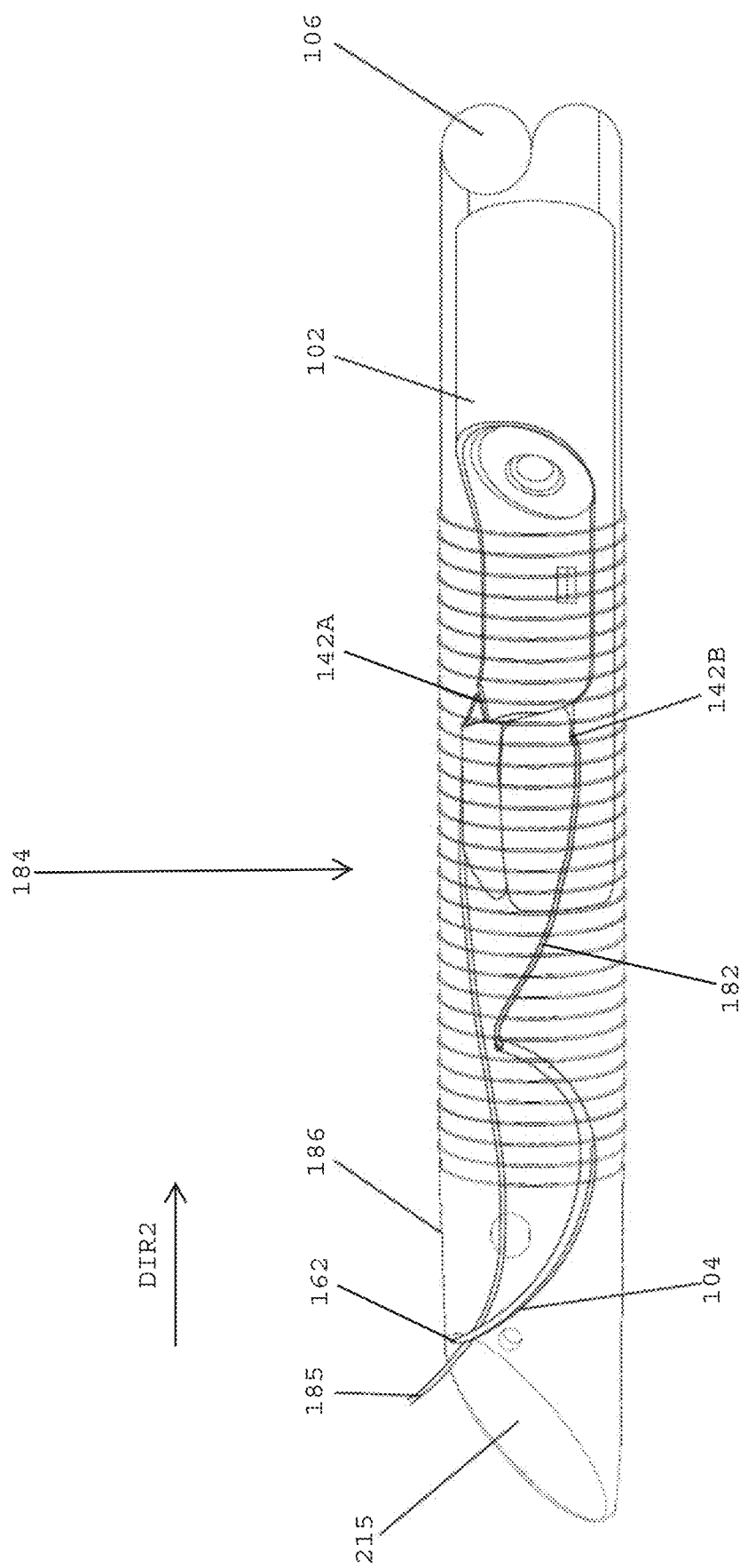
FIG. 15 illustrates a method of using the needle camera adaptor of FIGS. 12B and 14 for removing a curved surgical needle and a suture strand from a surgical site and removing the curved surgical needle and the suture strand through a trocar, in accordance with one embodiment of the present patent application.

Referring to FIG. 15, in one embodiment, the curved suture needle 104 and the suture strand 182 may be retracted through the conduit 215 of the elongated tube 186 of the cannula 184 (FIGS. 12A and 12B). The captured suture strand 182 preferably forms a friction fit with the suture retrieval slots 142A, 142B of the needle camera adaptor 102. The captured suture stand 182, the curved suture needle 104, and the needle camera adaptor 102 are preferably retracted through the conduit 215 in the direction designated DIR2, whereby the sharpened tip 162 trails away from the pulling direction DIR2. In this orientation, the curved suture needle 104 does not present a risk of damaging the expansible seal 190 located at the proximal end 188 of the cannula 184 (FIG. 12B).

Figure 16:
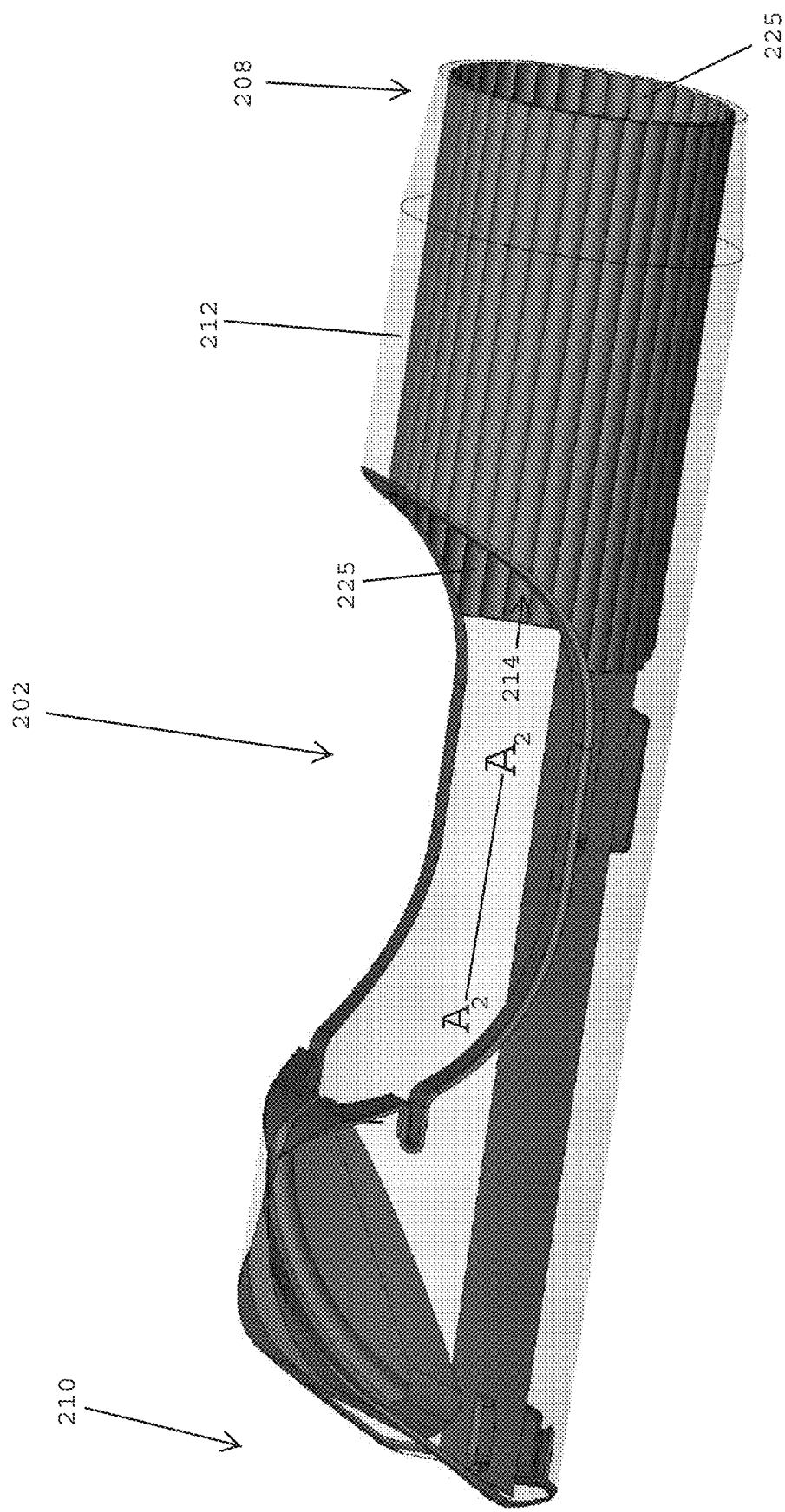
FIG. 16 is a perspective view of a needle camera adaptor having a proximal end with scalloped features, in accordance with one embodiment of the present patent application.

Referring to FIG. 16, in one embodiment, a needle camera adaptor 202 preferably has a proximal end 208 and a distal end 210. In one embodiment, the needle camera adaptor 202 preferably has an outer wall 212, such as a tube-shaped outer wall, that extends along the length of the needle camera adaptor between the proximal and distal ends 208, 210 thereof. The outer wall 212 may have a generally cylindrical shape and may have a varying thickness. In one embodiment, the needle camera adaptor 202 preferably has a central lumen 214 that extends along a central or longitudinal axis $A_2$ thereof. The lumen 214 preferably extends from the proximal end 208 to the distal end 210 of the needle camera adaptor. The central lumen 214 may be utilized for securing a distal end of an endoscope 106 (FIG. 1A) to the proximal end 208 of the needle camera adaptor 202 and/or for providing visual access to a suture needle as the combination of the needle camera adaptor and the suture needle are delivered through a cannula to a surgical site.

In one embodiment, adjacent the proximal end 208 of the needle camera adaptor 202, the tube-shaped outer wall 212 preferably includes an inner surface having castellated or scalloped features 225 for enabling the needle camera adaptor 202 to be secured to a distal end of an endoscope 106 (FIG. 1A) and/or for properly orienting the needle camera adaptor that is secured to the distal end of the endoscope. In one embodiment, the castellated or scalloped features 225 may be used to fine tune the amount of hoop stress and/or frictional forces that are needed to allow for easy attachment and removal of the needle camera adaptor 202 from the endoscope while still providing sufficient clamping force to enable the needle camera adaptor to remain attached to the endoscope as the needle camera adaptor is withdrawn from a surgical site through a trocar, cannula, or surgical tool.

In one embodiment, the proximal end of a needle camera adaptor (e.g., the tube-shaped outer wall adjacent the proximal end) may include a compressive material that grips onto the distal end of the cannula of the endoscope for forming a secure fit between the needle camera adaptor and the endoscope and/or for properly orienting the needle camera adaptor that is secured to the distal end of the endoscope.

While the foregoing is directed to embodiments of the present invention, other and further embodiments of the invention may be devised without departing from the basic scope thereof, which is only limited by the scope of the claims that follow. For example, the present invention contemplates that any of the features shown in any of the embodiments described herein, or incorporated by reference herein, may be incorporated with any of the features shown in any of the other embodiments described herein, or incorporated by reference herein, and still fall within the scope of the present invention.

What is claimed is:

1. A needle camera adaptor, comprising:
   an elongated body having a proximal end configured to be releasably attached to a distal end of an endoscope, a distal end, and a longitudinal axis that extends from the proximal end to the distal end, the elongated body including a tube-shaped outer wall that extends from the proximal end to the distal end of the elongated body;
   a lumen extending along the longitudinal axis of the elongated body from the proximal end to a distal opening in the distal end of the elongated body;
   a lateral access opening formed in the tube-shaped outer wall that provides lateral access to the lumen, wherein the lateral access opening is located in a central region of the elongated body that is between the proximal and distal ends of the elongated body;
   a needle securing channel formed in the tube-shaped outer wall of the elongated body that extends between the lateral access opening and the distal opening, wherein the needle securing channel extends along an axis that defines an oblique angle with the longitudinal axis of the elongated body, the lumen and the distal opening being configured to permit visualization of a needle and a surgical sight via a vision system of the endoscope;
   a proximal needle securing recess formed in an inner surface of the tube-shaped outer wall that is located within the central region of the elongated body;
   a distal needle securing recess formed in the inner surface of the tube-shaped outer wall that is located adjacent the distal end of the elongated body, wherein the axis of the needle securing channel extends between and is aligned with the proximal and distal needle securing recesses; and
   a curved suture needle having a proximal end with a suture attachment barrel, a distal end with a sharpened tip, and a curved elongated body extending from the proximal end to the distal end of the curved suture needle, wherein the proximal end of the curved suture needle is disposed within the proximal needle securing recess, the distal end of the curved suture needle is disposed within the distal needle securing recess, and the curved elongated body is disposed within the needle securing channel,
   wherein the proximal needle securing recess is off-set from the longitudinal axis of the elongated body, and wherein the distal needle securing recess is in alignment with the longitudinal axis of the elongated body.

2. The needle camera adaptor as claimed in claim 1, further comprising:
   a visualization device positioned within the lumen of the elongated body at the proximal end of the elongated body, wherein the lateral access opening and the needle securing channel are located within a field of view of the visualization device.

3. The needle camera adaptor as claimed in claim 2, wherein the visualization device comprises the endoscope.

4. The needle camera adaptor as claimed in claim 3, wherein the visualization device further comprises:
   a camera; and
   one or more lighting elements illuminating the field of view of the visualization device.

5. The needle camera adaptor as claimed in claim 1, wherein the needle securing channel comprises an elongated gap formed in the tube-shaped outer wall of the elongated body that extends from an outer surface to the inner surface of the tube-shaped outer wall, and wherein the needle securing channel includes one or more resilient elements that project into the gap that are adapted to provide a compressive three on lateral sides of the curved elongated body of the curved suture needle when the curved suture needle is disposed within the needle securing channel.

6. The needle camera adaptor as claimed in claim 5, wherein the curved elongated body of the curved suture needle that is disposed within the needle securing channel extends along the axis that defines the oblique angle with the longitudinal axis of the elongated body.

7. The needle camera adaptor as claimed in claim 1, further comprising:
   a distal stop located between the distal needle securing recess and the distal end of the elongated body preventing the sharpened tip of the curved suture needle from moving distal to the distal end of the elongated body.

8. The needle camera adaptor as claimed in claim 1, further comprising:
   a suture having a first end secured to the suture attachment barrel of the curved suture needle, wherein the suture extends through the lateral access opening and toward the proximal end of the elongated body of the needle camera adaptor.

9. The needle camera adaptor as claimed in claim 2, further comprising:
   at least one suture retrieval slot formed in the tube-shaped outer wall of the elongated body, wherein the at least one suture retrieval slot has an open end that is in communication with the lateral access opening and that faces toward the visualization device and a closed end that is distal to the open end, and wherein the at least one suture retrieval slot narrows between the open end and the closed end thereof.

10. The needle camera adaptor as claimed in claim 9, wherein the at least one suture retrieval slot is within the field of view of the visualization device.

11. The needle camera adaptor as claimed in claim 1, wherein the elongated body further comprises a sloping distal end face that extends between the distal end of the elongated body and a distal end of the needle securing channel.

12. A needle camera adaptor, comprising:
   a tube-shaped body having a proximal end, a distal end, and a longitudinal axis that extends from the proximal end to the distal end;
   a lumen extending along the longitudinal axis from the proximal end to an opening in the distal end of the tube-shaped body;
   a lateral access opening formed in an outer wall of the tube-shaped body that provides lateral access to the lumen, wherein the lateral access opening is located in a central region of the tube-shaped body that is between the proximal and distal ends of the tube-shaped body;
   a needle securing channel formed in the outer wall of the tube-shaped body that extends between the lateral access opening and the distal end of the tube-shaped body, wherein the needle securing channel extends along an axis that defines an oblique angle with the longitudinal axis of the tube-shaped body;
   a curved suture needle disposed within the needle securing channel and being removable from the tube-shaped body via the lateral access opening, wherein the needle securing channel and the curved suture needle extend along an axis that defines an oblique angle with the longitudinal axis of the tube-shaped body; and
   a visualization device positioned within the lumen at the proximal end of the tube-shaped body and facing toward the distal end of the tube-shaped body, wherein the lateral access opening, the needle securing channel, and the curved suture needle are located within a field of view of the visualization device and
   wherein the lumen and opening in the distal end are configured to permit visualization of the needle and a surgical sight via a vision system of an endoscope when the needle camera adaptor is coupled to the endoscope as desired.

13. The needle camera adaptor as claimed in claim 12, wherein the visualization device comprises:
   the endoscope having a distal end that is assembled with the proximal end of the tube-shaped body;
   a camera; and
   one or more lighting elements illuminating the field of view of the visualization device.

14. The needle camera adaptor as claimed in claim 12, further comprising:
   a proximal needle recess formed in an inner surface of the tube-shaped body that is located within the central region of the tube-shaped body and that is adapted to seat a proximal end of the curved suture needle; and
   a distal needle recess formed in the inner surface of the tube-shaped body that is located adjacent the distal end of the tube-shaped body and that is adapted to seat a distal end of the curved suture needle, wherein the axis of the needle securing channel extends between and is aligned with the proximal and distal needle recesses.

15. The needle camera adaptor as claimed in claim 14, wherein the curved suture needle includes the proximal end with a suture attachment barrel, the distal end with a sharpened tip, and a curved elongated body extending from the proximal end to the distal end of the curved suture needle, wherein the curved elongated body is disposed within the needle securing channel.

16. The needle camera adaptor as claimed in claim 12, further comprising:
   at least one suture retrieval slot formed in the outer wall of the tube-shaped body, wherein the at least one suture retrieval slot has an open end that is in communication with the lateral access opening and that faces toward the visualization device and a closed end that is distal to the open end, wherein the at least one suture retrieval slot narrows between the open end and the closed end thereof, and wherein the at least one suture retrieval slot is located adjacent a top side of the tube-shaped body.

17. A needle camera adaptor, comprising:
   a tube-shaped body having a proximal end, a distal end, and a longitudinal axis that extends from the proximal end to the distal end;
   a lumen extending along the longitudinal axis of the tube-shaped body from the proximal end to an opening in the distal end of the tube-shaped body;
   a lateral access opening formed in an outer wall of the tube-shaped body that provides lateral access to the lumen of the tube-shaped body, wherein the lateral access opening is located in a central region of the tube-shaped body that is between the proximal and distal ends of the tube-shaped body;
   a needle securing channel formed in the outer wall of the tube-shaped body that extends between the lateral access opening and the distal end of the tube-shaped body;
   a proximal needle securing recess formed in an inner surface of the outer wall, wherein the proximal needle securing recess is located within the central region of the tube-shaped body and is off-set from the longitudinal axis;
   a distal needle securing recess formed in the inner surface of the outer wall, wherein the distal needle securing recess is located adjacent the distal end of the tube-shaped body and is in alignment with the longitudinal axis, wherein the axis of the needle securing channel extends between and is aligned with the proximal and distal needle securing recesses;
   a curved suture needle having a proximal end with a suture attachment barrel, a distal end with a sharpened tip, and a curved elongated body extending from the proximal end to the distal end of the curved suture needle, wherein the proximal end of the curved suture needle is disposed within the proximal needle securing recess, the distal end of the curved suture needle is disposed within the distal needle securing recess, and the curved elongated body is disposed within the needle securing channel; and
   at least one suture retrieval slot formed in the outer wall of the tube-shaped body, wherein the at least one suture retrieval slot has an open end that is in communication with the lateral access opening and that faces toward the proximal end of the tube-shaped body and a closed end that is distal to the open end, wherein the lumen and opening in the distal end of the tube-shaped body being configured to permit visualization of the curved suture needle and a surgical sight via a vision system of an endoscope.

18. The needle camera adaptor as claimed in claim 1, wherein the needle securing channel is configured to releasably grip the needle placed therein.

\* \* \* \* \*

UNITED STATES PATENT AND TRADEMARK OFFICE
CERTIFICATE OF CORRECTION

PATENT NO. : 12,011,161 B2
APPLICATION NO. : 17/154088
DATED : June 18, 2024
INVENTOR(S) : Souls et al.

Page 1 of 1

It is certified that error appears in the above-identified patent and that said Letters Patent is hereby corrected as shown below:

In the Claims

Claim 5, Column 20, Line 40:
"compressive three on lateral sides of the curved elongated" should read "compressive force on lateral sides of the curved elongated".

Signed and Sealed this
Twenty-third Day of July, 2024

Katherine Kelly Vidal
*Director of the United States Patent and Trademark Office*